US012393660B2

(12) United States Patent
Fry

(10) Patent No.: US 12,393,660 B2
(45) Date of Patent: Aug. 19, 2025

(54) DNA ACCESS CONTROL SYSTEMS

(71) Applicant: The Government of the United States of America, as represented by the Secretary of Homeland Security, Washington, DC (US)

(72) Inventor: Mark Fry, Marco Island, FL (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 18/665,197

(22) Filed: May 15, 2024

(65) Prior Publication Data
US 2024/0386086 A1    Nov. 21, 2024

Related U.S. Application Data

(60) Provisional application No. 63/467,074, filed on May 17, 2023.

(51) Int. Cl.
*G06F 21/32* (2013.01)
*C12Q 1/6888* (2018.01)
(52) U.S. Cl.
CPC ........... *G06F 21/32* (2013.01); *C12Q 1/6888* (2013.01)
(58) Field of Classification Search
CPC ............................ G06F 21/32; C12Q 1/6888
See application file for complete search history.

(56) References Cited

U.S. PATENT DOCUMENTS

| | | |
|---|---|---|
| 5,543,294 A | 8/1996 | Silverstein et al. |
| 6,168,948 B1 | 1/2001 | Anderson et al. |
| 6,268,605 B1 | 7/2001 | Orava et al. |
| 7,430,046 B2 | 9/2008 | Jiang et al. |
| 7,465,545 B2 | 12/2008 | Kim et al. |
| 7,476,549 B2 | 1/2009 | Nahm et al. |
| 7,534,335 B2 | 5/2009 | Kennedy et al. |
| 7,790,118 B2 | 9/2010 | Maltezos et al. |
| 8,858,897 B2 | 10/2014 | Lim et al. |
| 9,134,207 B2 | 9/2015 | Zhou et al. |
| 9,512,479 B2 | 12/2016 | Kurnool et al. |

(Continued)

OTHER PUBLICATIONS

Tan, Eugene, et al. "Fully integrated, fully automated generation of short tandem repeat profiles." Investigative genetics 4 (2013): 1-15. (Year: 2013).*

(Continued)

*Primary Examiner* — Larry D Riggs, II
*Assistant Examiner* — Guozhen Liu
(74) *Attorney, Agent, or Firm* — Kelly G. Hyndman; Robert W. Busby

(57) ABSTRACT

An access control system and method configured to DNA-based identification to verify user identification. The access control system may be configured to access a database of biometric and biographic data. The database may comprise a biometric and biographic dataset associated with users. Matching logic may determine whether a user attempting to gain access to a secured location or system matches a dataset. The access control system may comprise a microfluidics device configured to perform DNA fingerprinting. The access control system may also comprise a silicone processor configured to execute the matching logic.

27 Claims, 15 Drawing Sheets

(56) References Cited

U.S. PATENT DOCUMENTS

| | | | |
|---|---|---|---|
| 10,724,084 | B2 | 7/2020 | Kordunsky et al. |
| 11,141,734 | B2 | 10/2021 | Handique et al. |
| 11,155,877 | B2 | 10/2021 | Sanders et al. |
| 11,179,482 | B2 | 11/2021 | Shabat et al. |
| 11,241,507 | B2 | 2/2022 | Shabat et al. |
| 11,249,000 | B2 | 2/2022 | Barrett et al. |
| 11,442,038 | B2 | 9/2022 | Boeke et al. |
| 2006/0006066 | A1 | 1/2006 | Yamazaki et al. |
| 2008/0131327 | A1 | 6/2008 | Van Dam et al. |
| 2009/0211911 | A1 | 8/2009 | Ohura et al. |
| 2010/0185871 | A1* | 7/2010 | Scherrer ............. G06F 21/6218 726/4 |
| 2010/0267023 | A1* | 10/2010 | Zabeau ................ C12Q 1/6855 435/6.12 |
| 2020/0094252 | A1 | 3/2020 | Chen et al. |
| 2020/0299139 | A1 | 9/2020 | Wu |

OTHER PUBLICATIONS

Skutkova, Helena, et al. "Advanced DNA fingerprint genotyping based on a model developed from real chip electrophoresis data." Journal of Advanced Research 18 (2019): 9-18. (Year: 2019).*

Bhargava, Akansha, and R. S. Ochawar. "Biometric access control implementation using 32 bit arm cortex processor." 2014 International Conference on Electronic Systems, Signal Processing and Computing Technologies. IEEE, 2014. (Year: 2014).*

Reidy, Thomas Martin, et al. "Transparency of PDMS based microfluidic devices under temperature gradients." Journal of Micromechanics and Microengineering 29.1 (2018): 015014. (Year: 2018).*

* cited by examiner

DNA ACCESS CONTROL SYSTEMS

CROSS-REFERENCES

This application claims the benefit of priority to U.S. Provisional Patent Application No. 63/467,074 filed May 17, 2023, incorporated by reference in its entirety.

STATEMENT OF GOVERNMENT INTEREST

The present invention was made by employees of the United States Department of Homeland Security in the performance of their official duties. The U.S. Government has certain rights in this invention.

FIELD

The invention relates generally to methods and systems for comparing a sample of DNA against samples in a database system for the purpose of determining or authenticating a user's identity.

BACKGROUND

There are many techniques for extracting DNA from a tissue sample. Scientists have found various ways to amplify and isolate portions of the DNA (microsatellites) for analysis and comparison. Because an individual's microsatellites are unique . . . . DNA fingerprinting is a useful technique for confirming an identity. In use, one would take a known sample of DNA and compare it against a proffered sample. If the samples match, it is highly likely the two DNA samples are from the same individual. Although the reliability of DNA matching can vary based on the quality of the sample and methods of preparation, some methods are more than 99% accurate.

Microfluidics is a field of science and technology that uses very small amounts of fluids and channels. It may be used for technology that can process low volumes of fluids to achieve multiplexing, automation, and high-throughput screening. Microfluidic systems may transport, mix, separate, or otherwise process fluids. Various applications rely on passive fluid control using capillary forces, in the form of capillary flow modifying elements, akin to flow resistors and flow accelerators. Other configurations may use external actuation such as rotary drives to apply centrifugal forces for the fluid transport.

SUMMARY

An example configuration may include an access control system for controlling access to a secure device (such as a computer or vehicle), secure facility (like a military base), or a secure location (such as an airport). The access control system may comprise an access control device that limits access to a secure device, secure facility, or secure location. To gain access, a user may present biometric data and/or biographic data to the access control system. The access control system may perform a matching process of the proffered biometric and/or biographic data against biometric data and/or biographic data stored in a database. If the access control system determines a proffered biometric data and/or biographic data matches the stored biometric data and/or biographic data, the access control system can cause the access control device to change from a first state to a second state. For example, if the access control device is a magnetic lock on a door, the access control system can cause the magnetic lock to switch from a locked state to an unlocked state, granting access to the user to a secure facility.

The access control system may comprise a microfluidic chip, a processor, a database and access control device. In some configurations, the chip assembly, processor, access control device, and database are separate components connected through networking components (system bus, internet, Bluetooth, etc.) Two or more of these components may be built into a single device. For example, the chip assembly and processor may be installed into the access control device directly.

The microfluidic chip may comprise a tissue sample collector, electrophoresis station, probe labelling station, and a detector (such as a probe detector). The tissue sample collector may be configured to collect cells such as blood cells, check cells, saliva, hair cells, or skin cells. The tissue sample collector may provide the tissue sample to a DNA extractor. The DNA extractor may be configured to extract DNA from the cells. The DNA amplification station may be configured to amplify the DNA. The electrophoresis station may be configured to create DNA bands. The bands may comprise a plurality of minisatellites having similar lengths. The probe labelling station may be configured to bind probes to the bands in the membrane. The detector may be configured to detect presence or absence of probes in the membrane. The detector may be configured to generate a first dataset of the bands.

The access control system may comprise a processor configured to: obtain the first dataset from the detector, a copy of the first dataset, or information about the first dataset; and provide the first autoradiograph from the detector, a copy of the first autoradiograph, or information about the first autoradiograph to the comparison logic.

The database and/or the processor may comprise matching logic configured to determine the first dataset matches, within a match threshold, a second dataset obtained from a database of preexisting datasets; and device logic configured to cause a state of a device to change from a first state to a second state.

Some configurations of the access control system may comprise a power source configured to provide electricity to the DNA fingerprinting device. The power source may comprise a microfluidics power source configured to provide power to components in the microfluidics chips. The fingerprinting device may comprise a power source configured to provide electricity to the processor. The access control device may also comprise a power source. In some configurations, the power source powers multiple components (chip assembly, processor, database, and access control device). In other configurations, the power source powers two or three of these components. For example, in some configurations the chip assembly and processor share the same power source.

The access control system may comprise a wash station configured to the wash the microfluidics chip.

The device logic may be configured to display the first dataset on a tangible display; store the first dataset in the database; export a control signal to a barrier, gate, or a lock to cause it to open or close; grant or deny access to a computer or a physical location; or display a symbol designating whether the user's asserted identity matches a dataset within the database.

The processor may comprise a biographic verification logic comprising a biographic information collector configured to collect a first biographic information from the user; a biographic association logic configured to associate the first biographic information with the first dataset. The database may be configured to store biographic information associated with previously stored datasets. The biographic verification logic may comprise verification logic configured to verify that second biographic information associated with the second dataset matches the first biographic information associated with the first dataset; and mark the user as verified for a time period.

Some configurations of the invention may include a method of performing RFLP (restriction fragment length polymorphism) based fingerprinting. The steps may comprise collecting a tissue sample from a user; providing the tissue sample to a DNA extractor; extracting DNA from the sample using a DNA extraction technique; and performing RFLP based DNA fingerprinting by performing restriction digestion. The method may involve using restriction enzymes such as Eco R1 5' GAATTC 3' to create different fragments. The fragments may comprise a plurality of lengths. The lengths of the fragments may be generally different in different individuals. The method may comprise performing electrophoresis to creates bands of DNA. The bands may comprise a plurality of DNA fragments. Each band may comprise a plurality of DNA fragments that have similar lengths. Electrophoresis may be performed in an electrophoresis station with using an agarose gel comprising pores. The electrophoresis station may have an anode and a cathode to cause the DNA fragments to flow through the agarose gel. The pores of the gel slowing the movement of the longer fragments more than the shorter fragments such the bands having the longer fragments appear closer to the starting section. The bands may be transferred to a membrane using southern blotting technique. The method may involve binding probes to the DNA fragments; autoradiographing the membrane containing the bands and probes to generate a first autoradiograph of the bands; determining the first autoradiograph matches a second autoradiograph from a database of preexisting autoradiographs; and executing a match successful process configured to cause a state of a device to switch from a first state to a second state.

A configuration of the present invention may comprise an access control system comprising a microfluidic chip for RFLP (restriction fragment length polymorphism) DNA fingerprinting comprising a tissue sample collector configured to collect cells such as blood cells, check cells, saliva, hair cells, or skin cells. The tissue sample collector may provide the tissue sample to a DNA extractor.

The access control system may comprise a DNA extractor configured to extract DNA from the cells. Some configurations may comprise a restriction digestor configured to perform restriction digestion using restriction enzymes to create minisatellites. The minisatellites may comprise repetitive non-coding short DNA sequences of 10-60 based pairs.

The access control system may comprise an electrophoresis station configured to create bands of DNA. The bands may comprise a plurality of minisatellites having similar lengths. The access control system may also comprise a transfer station configured to transfer the bands to a membrane.

The access control system may comprise a probe labelling station configured to bind probes to the bands in the membrane. The probe labelling station may comprise a probe wash station configured to wash excess probes from the membrane.

The access control system may comprise a detector such as an autoradiography station configured to irradiate the membrane containing the bands and probes to generate a first autoradiograph of the bands.

The access control system may comprise a processor comprising matching logic configure to determine the first autoradiograph matches, within a match threshold, a second autoradiograph obtained from a database of preexisting autoradiographs; and device logic configured to cause a state of a device to change from a first state to a second state.

In another configuration, a method of performing PCR based DNA fingerprinting is provided. The method may comprise collecting a tissue sample; providing the tissue sample to a DNA extractor; extracting a DNA sample from the tissue sample using a DNA extraction technique; binding labelled STR primers with a polymerize chain reaction to the DNA sample to amplify the DNA fragments and form labelled STRs (short tandem repeats). Probes or labels comprising fluorescein or rhodamine may be used. The method may involve performing electrophoresis to form labelled STR bands using an electrophoresis station. Various detection methods may be used. For example, the bands may be fluoresced using a laser. A detector may be used to detect reflected light from the labelled primers bound to the bands. The detector may generate a first dataset. The first dataset may show a frequency of light reflected and a relative position. The relative position may be based on the distance the STRs travelled during electrophoresis. The dataset may be unique to each individual. A processor may determine the first dataset matches a second dataset from a database of preexisting datasets within a match threshold. The processor may execute a match successful process configured to cause a state of a device to switch from a first state to a second state.

Another configuration of the invention may comprise an access control system comprising a microfluidic chip and a processor for PCR-based DNA fingerprinting. The microfluidic chip may comprise a tissue sample collector configured to collect cells such as blood cells, check cells, saliva, hair cells, or skin cells; the tissue sample collector may provide the tissue sample to a DNA extractor; the DNA extractor may be configured to extract a DNA sample from the cells; a priming station may be configured to bind labelled STR primers with a (PCR) polymerize chain reaction to the DNA sample to amplify the DNA fragments and form labelled STRs (short tandem repeats); an electrophoresis station may be configured to create bands of DNA; the bands may comprise a plurality of minisatellites having similar lengths; a laser assembly may be configured to illuminate the bands of DNA with laser light of different frequencies; and a detector may be configured to detect reflected light from the labelled primers bound to the bands. The detector may be configured to generate a first dataset; the first dataset may be configured to show the frequency of light reflected and a relative position. The relative position may be based on the distance the STRs travelled during electrophoresis. The dataset may be unique to each individual.

DETAILED DESCRIPTION

DNA Extraction Techniques

Figure 1A:
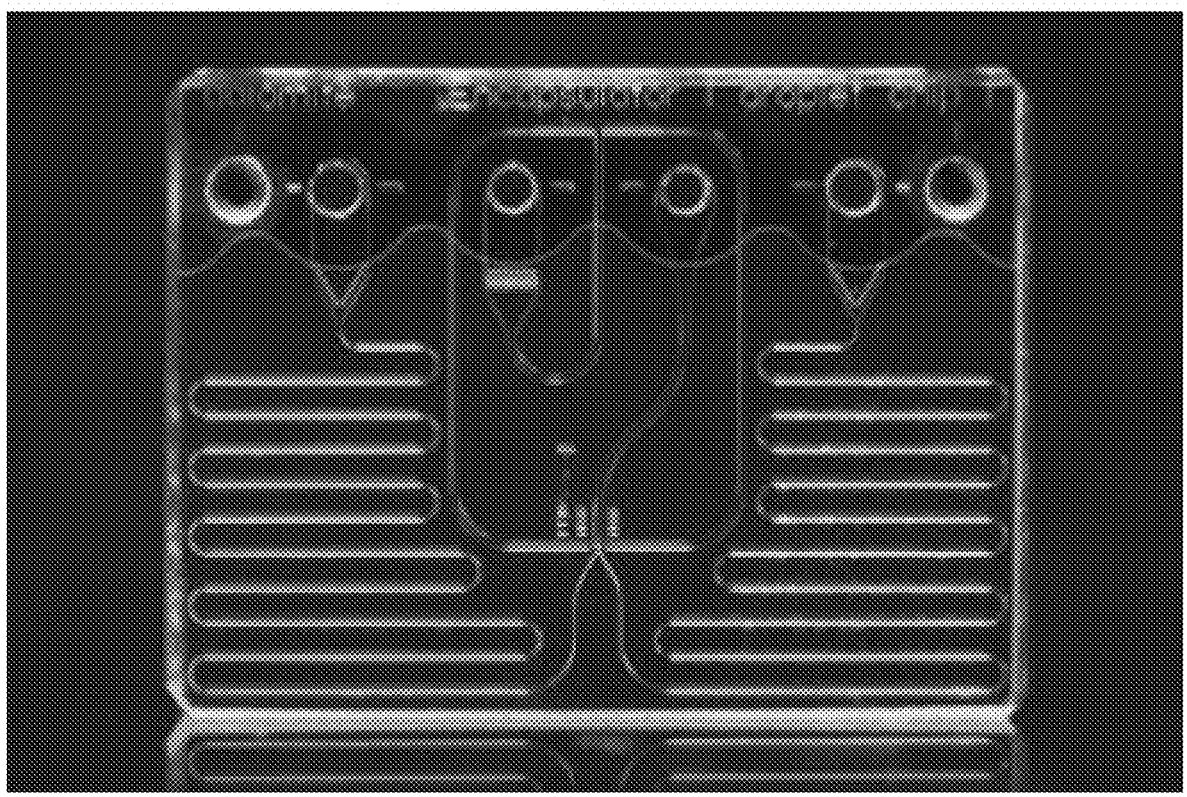
FIGS. 1A & 1B are photographs of microfluidic chips. The microfluidics chip may be configured depending on its functionality. The structure and design of the microfluidics chip may be adjusted so that the chip is configured to accomplish certain functions.

There are many known DNA extraction techniques such as DNA extraction techniques include organic extraction (phenol-chloroform method), nonorganic method (salting out and proteinase K treatment), and adsorption method (silica-gel membrane). Other commercially known DNA extraction techniques include GenFind, MagMax, DNA Xtractor, QIAamp, Puregene, Cobas, PCI, PCI w/PLG. U.S. Pat. No. 11,155,877 incorporated by reference in its entirety discloses various methods and systems for DNA extraction. Another know method is the Boom nucleic acid extraction method which is described in U.S. Patent Application Publication No. 2020/0299139 incorporated by reference in its entirety.

DNA Amplification

There are many methods of DNA amplification technology such as VNTR analysis, STR analysis, CTR analysis, Restriction Fragment Length Polymorphism (RFLP) analysis, allele specific oligonucleotide (ASO) analysis, denaturation temperature analysis, single strand conformation polymorphism (SSCP) analysis, amplified fragment-length polymorphism (AFLP) analysis, microsatellite or single-sequence repeat (SSR) analysis, rapid-amplified polymorphic DNA (RAPD) analysis, sequence tagged site (STS) analysis or a combination thereof. Systems and methods for DNA amplification are discussed in U.S. Pat. No. 9,512,479 incorporated by reference in its entirety. U.S. Pat. No. 5,543,294 incorporated by reference in its entirety discloses RFLP fingerprinting.

Polymerase Chain Reaction is another system and method for amplifying DNA in a sample. There are many methods such as: Conventional (qualitative) PCR, Multiplex PCR, Nested PCR, Reverse transcriptase PCR and Quantitative Real-time PCR, Quantitative PCR, Hot-start PCR, Touchdown PCR, Assembly PCR, Colony PCR, Methylation-specific PCR, LAMP assay, and real-time PCR, etc. Multiplex PCR may be used to amplify multiple targets in a single PCR permitting their simultaneous analysis. Nested PCR may be a modified PCR method intended to decrease nonspecific binding of products because of amplification of unexpected primer-binding sites. This method may involve two PCR steps. In the first PCR reaction, one pair of primers is used to produce DNA products, which act as a target for the second PCR reaction. The reaction helps to increase the specificity of DNA amplification. Reverse transcriptase PCR (RT-PCR) may involve mRNA as the starting material and use reverse transcriptase to convert mRNA into the complementary DNA (cDNA). This cDNA is then amplified with the help of regular PCR. Quantitative PCR may be used to quantitate the amount of target DNA (or RNA) in a particular sample. Hot-start PCR may decrease nonspecific amplification of DNA at lower temperature steps of PCR. Reaction components are manually heated before adding Taq polymerase to the DNA-melting temperature (i.e., 95° C.). Touchdown PCR may involve annealing temperature during the first two cycles of amplification is set at approximately 3-10° C. above estimated Tm (optimal melting temperature) and the temperature is slowly decreased in the subsequent cycles. Higher annealing temperature in two initial cycles leads to more specificity for primer binding, and the lower temperatures allow more efficient amplification later on. Assembly PCR may be useful for synthesis of long DNA segments by doing PCR on a pool of long oligonucleotides that has short overlapping segments and in turn assembling more DNA segments into one segment. Methylation specific PCR may involve sodium bisulfite treatment and is used to identify patterns of DNA methylation at cytosine guanine islands in genomic DNA. LAMP assay (loop-mediated isothermal amplification) may use 3:6 primer sets, one of which is a loop-like primer. This technique utilizes Bst-polymerase. Real-time PCR may allow quantitative estimation of PCR product, as the amplification progresses. It uses nonspecific dye such as SYBR® green I or fluorescence resonance energy transfer.

Electrophoresis

Electrophoresis is a laboratory technique used to separate DNA, RNA or protein molecules based on their size and electrical charge. Electrophoresis is used in laboratories to separate macromolecules based on size. The technique applies a negative charge to agarose gel. Because DNA is negatively charged, DNA fragments will flow through the gel towards the positive electrode. Electrophoresis is used extensively in DNA, RNA and protein analysis. Equipment, processes, and logic for electrophoresis and electrophoresis stations may be implemented as set forth in the following patents and patent applications.

U.S. Pat. No. 11,442,038 incorporated by reference in its entirety discloses an automated capillary electrophoresis system.

U.S. Patent Application Publication No. 2009/0211911 incorporated by reference in its entirety discloses a capillary electrophoresis apparatus.

U.S. Patent Application Publication No. 2006/0006066 incorporated by reference in its entirety discloses a capillary electrophoresis apparatus.

U.S. Pat. No. 7,534,335 incorporated by reference in its entirety discloses a multiplexed, absorbance-based capillary electrophoresis system.

Restriction Digestion Using Restriction Enzymes

Restriction digestion also called restriction endonuclease is a process in which DNA is cut at specific sites, dictated by the surrounding DNA sequence. Restriction digestion is accomplished by incubation of the target DNA molecule with restriction enzymes-enzymes that recognize and bind specific DNA sequences and cleave at specific nucleotides either within the recognition sequence or outside of the recognition sequence. Restriction digestion can result in the production of blunt ends (ends of a DNA molecule that end with a base pair) or sticky ends (ends of a DNA molecule that end with a nucleotide overhang). Restriction digestion is usually used to prepare a DNA fragment for subsequence molecular cloning, as the procedure allows fragments of DNA to be pieced together like building blocks via ligation. The results of a restriction digestion can be evaluated by gel electrophoresis, in which the products of the digestion are separated by molecule length (based on the negative charge of DNA molecules) in a polymer gel to which an electric field has been applied. The components of a typical restriction digestion reaction include the DNA template, the restriction enzyme of choice, a buffer and sometimes BSA protein.

Restriction digestion is a process of cutting DNA molecules into smaller pieces with special enzymes called Restriction Endonucleases (sometimes just called Restriction Enzymes or RE's). These special enzymes recognize specific sequences in the DNA molecule (for example GATATC) wherever that sequence occurs in the DNA. Restriction digestion begins by mixing the DNA and the RE.

Southern Blotting Technique

A Southern blot or Southern blotting is a laboratory method that may be to detect specific DNA molecules from among other DNA molecules. The technique was named after its inventor, Edward Southern.

The first step in a Southern blot is to prepare the DNA mixture by breaking it into small fragments using a protein called a restriction enzyme. The mixture of DNA fragments may then be separated according to size by way of a technique called gel electrophoresis. Following separation, the double-stranded pieces of DNA may be denatured, or separated, into single strands within the gel. Next, the DNA may be transferred from the gel onto a blotting membrane. Although this step (transferring to a membrane) is what gives the technique the name "Southern blotting," the term also can be used to describe the entire procedure.

Once the transfer is complete, the membrane carries all the bands originally on the gel. The membrane is then treated with a small piece of DNA or RNA called a probe, which has been designed to have a sequence that is complementary to a particular DNA sequence in the sample; this allows the probe to hybridize, or bind, to a specific DNA fragment on the membrane. In addition, the probe has a label, which may be a radioactive atom or a fluorescent dye. Thus, following hybridization, the probe permits the DNA fragment of interest to be detected with detector from among the many different DNA fragments on the membrane.

Probe Labelling

Southern blotting may use labelled probes. The labelled probes hybridize with complementary single stranded nucleic acids with each other to form double stranded molecules. Examples of probe labelling techniques may include PCR labeling, Nick translation, random oligo primed synthesis, and end labeling. These techniques may be used in certain configurations of the invention.

PCR labeling is a technique of incorporating labeled nucleotides into a probe. Design primers that will amplify a sequence to use as a probe, and simply include a labeled Deoxynucleotide triphosphates (dNTP) during PCR.

Nick translation is a tagging technique where DNA polymerase I is used to replace some of the nucleotides of a DNA sequence with their labeled analogues. In this process, DNA molecules are first treated with DNase to produce single-stranded "nicks". Then DNA polymerase I elongates the 3' hydroxyl terminus of the nicked sites, removing nucleotides by 5'-3' exonuclease activity and replacing them with modified dNTPs, thus labeling the DNA molecule. This technique is commonly used in fluorescence in situ hybridization (FISH) to label the probes.

Random primed labeling is a method of incorporating radioactive nucleotides along the length of a fragment of DNA. Random primed labeling can give specific activities of between $2\times10$ (9) and $5\times10$ (9) dpmo/µg. In the method a DNA fragment is denatured by heating in a boiling water bath. Then, random sequence oligonucleotides are annealed to both strands. Klenow fragment polymerase is then used to extend the oligonucleotides, using three cold nucleotides and one radioactively labeled nucleotide provided in the reaction mixture, to produce a uniformly labeled double-stranded probe. Since each batch of random oligonucleotides contains all possible sequences, any DNA template can be used with this method.

End labeling is a technique in which the end of a DNA (or RNA) molecule is specifically labeled. The 5' end can be labeled with the enzyme polynucleotide kinase, which donates the terminal (gamma) phosphate group (usually radioactive 32 P) from a dNTP to the 5' OH. Since only one marked residue per probe molecule is incorporated by this method, the specific activity of the label (radioactive counts per minute per microgram of DNA) is lower than some other methods. The 3' ends can also be labeled, with terminal transferase; this enzyme can add a small chain of identical labeled nucleotides, so it gives higher specific activity than the 5' method, but it may create potentially undesirable new sequence in the probe.

Probe Detection

A detector may take the form of an imaging station (a station for detecting probes) configured to detect probes attached to the DNA. The detector may be configured to generate a dataset of the detected probes. A dataset may be a report, table, image or graph of the detected probes. There are many ways of performing probe detection. For example, probe detection may be performed by autoradiography, colorimetric, fluorescent, and chemiluminescent detection systems and methods. Each detection system has certain advantages and disadvantages in a given setting. Some detection systems are very sensitive and some less sensitive.

In autoradiography, radioactive labeled probes are detected using X-ray film. Typically, the probes have a short half-life (about 2 weeks). So, the probes cannot be stored for a long time. Since the probes are radioactive, the lab performing radiograph typically has radioactive material handling procedures and be equipped to dispose of radioactive materials. Autoradiography can, for example, be used to analyze the length and number of DNA fragments after they are separated from one another by a method called gel electrophoresis. U.S. Pat. No. 11,249,000 incorporated by reference in its entirety provides autoradiography methods and systems for imaging via the detection of alpha particles, beta particles, or other charged particles. U.S. Pat. No. 6,268,605 incorporated by reference in its entirety provides a method of autoradiography imaging.

Colorimetric detection generally involves the production of a colored precipitate which can be seen with the naked eye. In a typical system, the DNA probe itself is labeled with an antigen such as digoxigenin; following hybridization to its target it would be exposed to an anti-digoxigenin antibody conjugated to an enzyme capable of catalyzing a colorimetric reaction. One commonly used example is alkaline phosphatase which will act on substrates NBT & BCIP to produce a dark purple product.

Fluorescent detection may involve probes which are directly labeled with fluorophores. Fluorescing may involve probes which are coupled to fluorescent molecules indirectly. For example, if a probe is labeled with biotin, it would be exposed to avidin conjugated to a fluorescent tag. (Biotin and avidin strongly and specifically bind together, like an antibody and its antigen.) Fluorophores emit light when excited by light of an appropriate wavelength. An imaging station may comprise a fluorescent detection station. A fluorescent detection station may comprise a laser assembly and a detector for example. Fluorescein and rhodamine based probes may be used for fluorescent detection/detector based embodiments.

Chemiluminescence involves an enzymatic reaction that triggers the release of ordinary visible light. Chemiluminescence is an efficient diagnostic tool for biosensing and bioimaging. In contrast to fluorescence, chemiluminescence does not require irradiation by an external light source, and as a result, the background signal is extremely low and the obtained sensitivity is considerably enhanced. Triggerable phenoxy-dioxetanes are often used as the light emission of these compounds can be generally initiated by deprotection of various substrates. However, the power of the chemiluminescence emission of these compounds in aqueous conditions may reduce their use in bioassays without additives. Effective probes in terms of signal-to-noise ratio can be obtained by equipping our phenoxy-dioxetane luminophores with enzymatic responsive groups composed of peptide substrates. Such compounds are highly stable to spontaneous hydrolysis and, therefore, do not produce any background signal. Various chemiluminescent probes can used in various configurations of the invention. For example, U.S. Pat. No. 11,179,482 incorporated by reference in its entirety discloses chemiluminescent probes for diagnostics and in vivo imaging. U.S. Pat. No. 11,241,507 incorporated by reference in its entirety discloses multi-assay microfluidic chips that can use chemiluminescent probes.

Minisatellites

A minisatellite is a tract of repetitive DNA in which certain DNA motifs/repeated patterns (ranging in length from 10-60 base pairs) are typically repeated 5-50 times. Minisatellites occur at more than 1,000 locations in the human genome, and they are notable for their high mutation rate and high diversity in the population.

Minisatellites are prominent in the centromeres and telomeres of chromosomes, the latter protecting the chromosomes from damage. The name "satellite" refers to the early observation that centrifugation of genomic DNA in a test tube separates a prominent layer of bulk DNA from accompanying "satellite" layers of repetitive DNA. Minisatellites are small sequences of DNA that do not encode proteins but appear throughout the genome hundreds of times, with many repeated copies lying next to each other.

Minisatellites are longer and microsatellites are shorter. Throughout this patent application minisatellites are alternatively referred to as variable number tandem repeats (VNTR) and microsatellites are short tandem repeats (STR) or simple sequence repeats (SSR). Technically both minisatellites and microsatellites are variable number of tandem repeats DNA.

Fluorescence detectors are devices configured to measure intensity and/or local of DNA bands that have bound fluorescence probes. In configurations using a fluorescence detector, the structure and design of the fluorescence detector may include some of or all of the design, process, and/or configurations set forth in the following patents.

U.S. Pat. No. 7,476,549 incorporated by reference in its entirety discloses a laser-induced fluorescence detection device and method. U.S. Pat. No. 7,430,046 incorporated by reference in its entirety discloses a pathogen and particle detector system and method. U.S. Pat. No. 11,141,734 incorporated by reference in its entirety discloses a fluorescence detector for microfluidic diagnostics. U.S. Pat. No. 10,724,084 incorporated by reference in its entirety discloses systems and methods for fluorescence detection with a movable detection module.

Microfluidics Chip

Figure 1B:
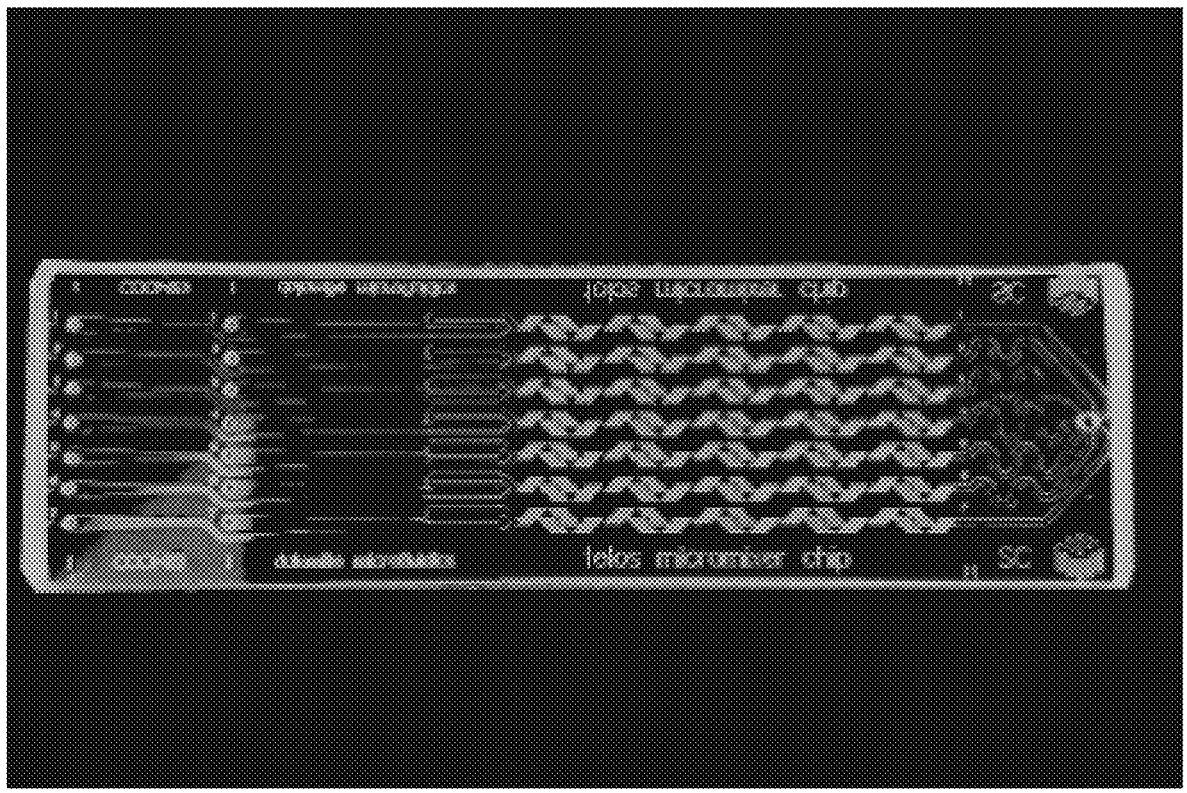

FIGS. 1A and 1B illustrate an example of a microfluidics chips. The microfluidics chip of the present invention can take various forms, have various structural details, and can execute various functions. Aspects of certain configurations of the present invention may use one or more of the methods, configurations, and details of the microfluidics chips disclosed in the following U.S. patents and U.S. Patent Publications. U.S. Patent Application Publication No. 2008/0131327 incorporated by reference in its entirety relates to method of fluid interchange in microfluidic chips. U.S. Pat. No. 7,790,118 incorporated by reference in its entirety relates to a microfluid chip with a membrane. U.S. Pat. No. 6,168,948 incorporated by reference in its entirety relates to miniaturized genetic analysis system and methods. U.S. Pat. No. 8,858,897 incorporated by reference in its entirety relates to a microfluidic chip for analysis for fluid sample. U.S. Pat. No. 7,465,545 incorporated by reference in its entirety relates to a microfluidic chip and manipulating apparatus having the same. U.S. Patent Application Publication No. 2020/0094252 incorporated by reference in its entirety relates to a microfluidic chip for separating and detecting whole blood sample. U.S. Pat. No. 9,134,207 incorporated by reference in its entirety relates to a microfluidic chip and assay system.

FIG. 1A shows a fluorophilic two reagent droplet chip 1 configured to enable 2-reagent droplets containing biological material to be generated with ease. An output droplet size in the range Ø30 μm-Ø70 μm can typically be selected with high monodispersity. This chip can be configured to interface directly with a sample reservoir chip via an FKM gasket. When being used, two reagent streams meet immediately before the junction, minimizing mixing prior to the formation of droplets.

FIG. 1B shows a micromixer chip 20. The chip may be made of glass and configured to rapidly mix two fluid streams. The chip may be built in hydrophilic and hydrophobic configurations. A micromixer chip may be included to provide mixing for reaction kinetics, sample dilution, improving reaction selectivity, rapid crystallization, micro and nanoparticle synthesis and fluid emulsification.

A chip assembly may comprise one or more microfluidics chips. The chip assembly may comprise connection hardware such as various tubing, valves, O-rings, plugs, seals, fittings, valve controllers, and connectors. The chip assembly may comprise one or more microfluidic components. Microfluidic components may include pumps, reservoirs, cleaning reagents, chemicals, temperature control units, microscopes, flow rate sensors, sensor displays, etc. A pump may be connected to the microfluidic chip to provide pressurized air to the microfluidic chip. For example, some pumps may provide pressures of 500 mbar above atmospheric pressure. A computer or chip controller may control the pumps. A temperature control unit may be configured to provide heat, remove heat, provide cooling to chemicals, samples, and/or reagents in the chip assembly. A temperature control unit may be configured to maintain temperatures of chemicals, samples, and/or reagents in the chip assembly.

Various chemicals may be used in the chip assembly. A first chemical may be an emulsion stabilizer for aqueous droplets in fluorinated oil. The first chemical may be a block copolymer configured to stabilize emulsions due to its amphiphilic polymer blocks. Other chemicals may be provided to enhance droplet formation rates & sizes. Some chemicals may be configured to stabilize emulsions. Other chemicals may break emulsions and emulsion droplets.

Access Control System

Figure 2:
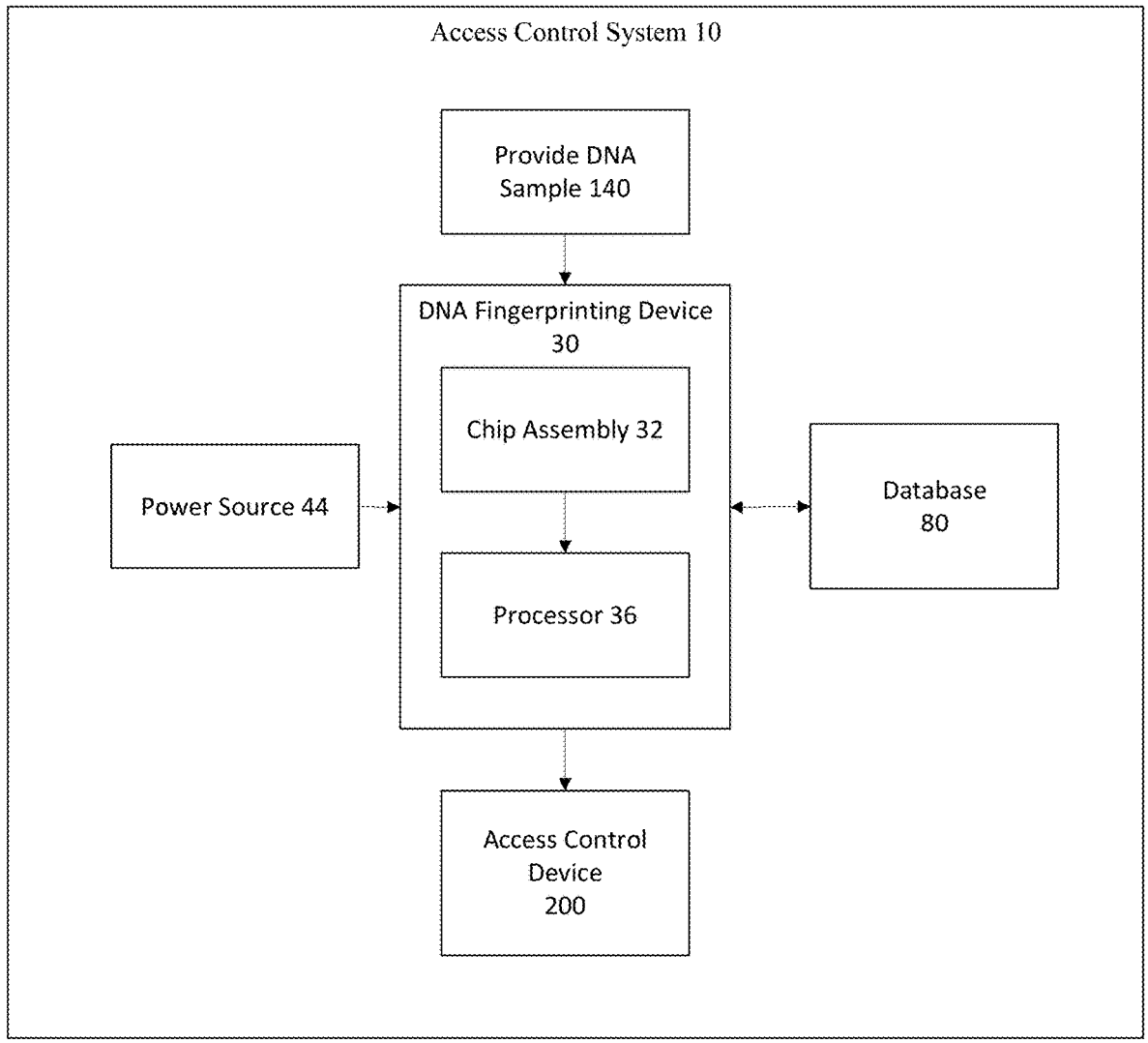
FIG. 2 illustrates an access control system. The access control system may comprise a chip assembly and a processor. The chip assembly may be a microfluidics chip molded from PDMS (Polydimethylsiloxane) or PMMA. The processor may be a microprocessor optionally made from silicone.

FIG. 2 illustrates an access control system 10. The access control system 10 may comprise a chip assembly 32 and a processor 36 (collectively the "DNA Fingerprinting Device 30"). A user may provide a DNA sample 140 to the chip assembly 32. The chip assembly 32 may comprise a microfluidics chip molded from PDMS (Polydimethylsiloxane) or PMMA. The processor 36 may be a microprocessor. The microprocessor may be made from silicone. The chip assembly may be configured to generate an image of processed DNA strands (DNA bands). The image may be an electronic image (like JPG, PNG, etc.) file. The image may be in a proprietary data format. The chip assembly may generate multiple images such as a first image, second image, etc. The chip assembly may generate one or more images of DNA bands of a first user, second user, etc. The image of the DNA band may comprise biometric data.

The processor may be configured to transform the image into a first dataset. The first dataset may identify or be associated with a first user. The first dataset may be a representation of the first user's DNA. The dataset may comprise biometric data such as images, mathematical representations of images, or other data of DNA, fingerprints, voiceprints, facial images, etc. The first dataset may also comprise an identifier, metadata, and biographic information. Biographic information may comprise a name, email, address, phone number, birth date, birth city, etc. The processor may be configured to generate one or more datasets associated with a user. The processor may be configured to store the one or more datasets in a database.

FIG. 2 shows an embodiment wherein the access control system comprises a database 80. The database may comprise a plurality datasets, each dataset may be associated with a user identity. The database may comprise a second dataset that matches the first dataset, optionally within a threshold value. The processor may be configured to instruct the access control device to change from a first state to a second state based on whether the matching logic determines the first dataset from the user matches the second dataset in the database. The database or the processor may comprise and execute the matching logic.

Chip Assembly

Figure 4:
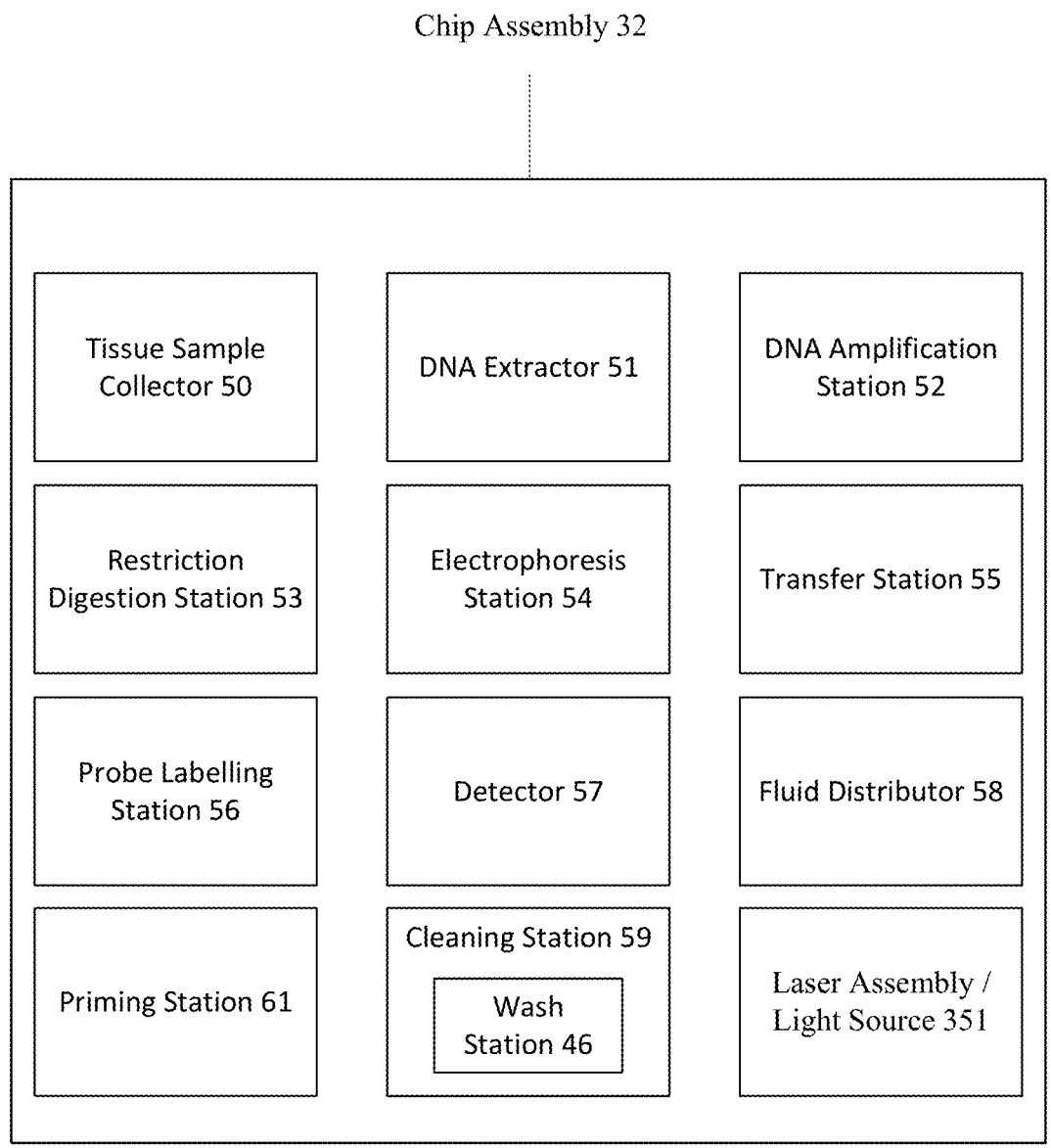
FIG. 4 shows a chip assembly that may be configured to perform PCR based DNA fingerprinting. More specifically, the microfluidic chip of FIG. 4 may be configured to generate a dataset of DNA bands.

As shown in FIG. 4, the chip assembly may be a microfluidics chip. The chip assembly may comprise several components such as a tissue sample collector 50, a DNA extractor 51, a DNA amplification station 52, a DNA restriction digestion station 53, an electrophoresis station 54, a transfer station 55, a probe labelling station 56, a detector 57 (such as an autoradiography station, colorimetric station, fluorescent station, and chemiluminescent station), a fluid distributor 58, and a cleaning system 59. The cleaning system may comprise a heating element for disinfecting the tissue sample collector and other parts of the microfluidics chip. The cleaning system may comprise a wash station 46. The wash station 46 may comprise an irrigation system for cleaning components of the microfluidics chip. The wash station may comprise an evaporator for evaporating liquids from the sample receiving surface. The wash station may comprise channels, tubes, and pumps designed to optimize buffer volume, channel flow, wash cycles, manifold flow distribution, heat exchange, and/or pump and valve operation.

Figure 3:
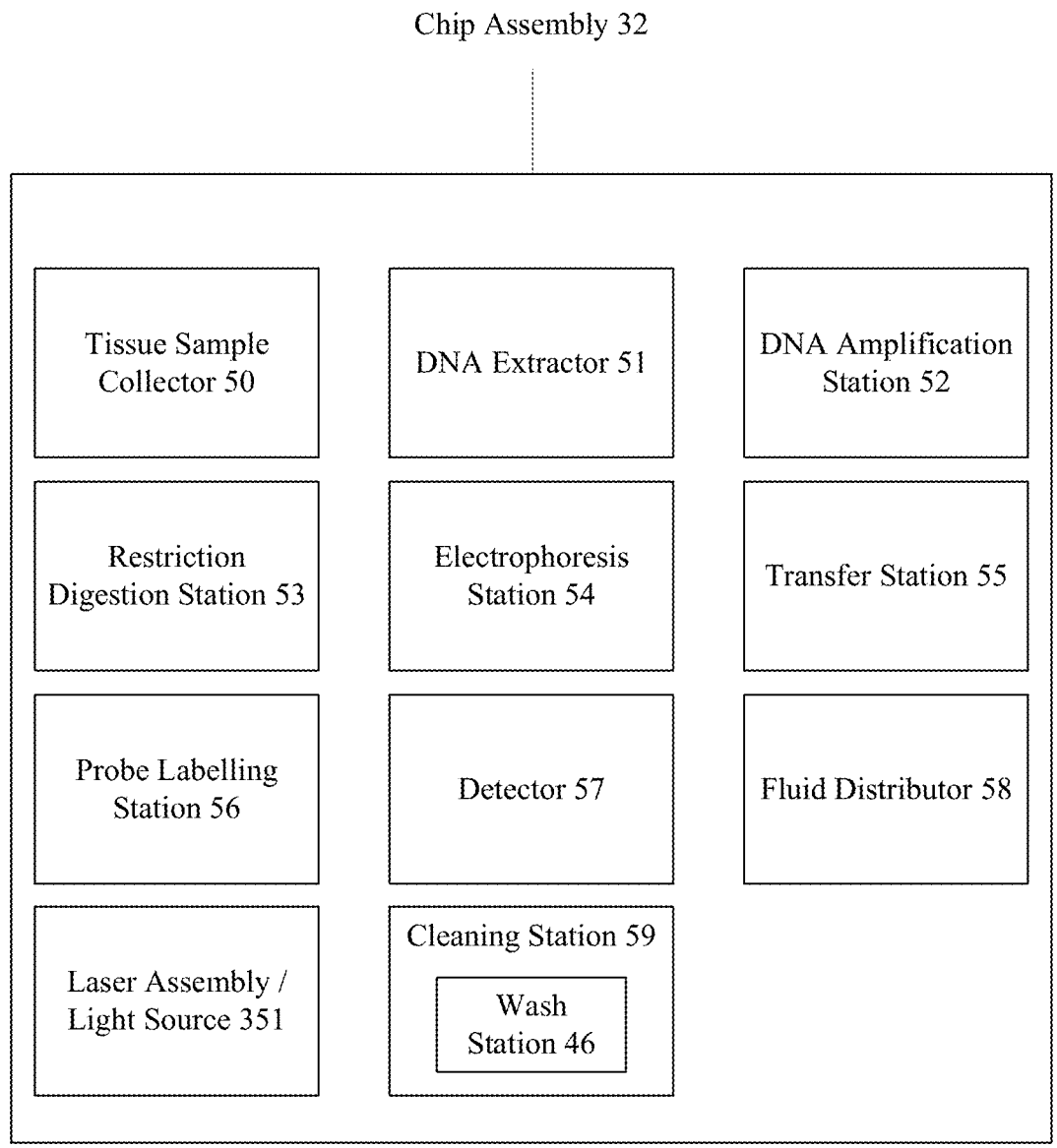
FIG. 3 shows a chip assembly that may be configured to perform RFLP based DNA fingerprinting. More specifically, the microfluidic chip of FIG. 3 may be configured to generate a dataset of DNA bands.

The microfluidics chips of FIG. 3 may be configured to perform RFLP fingerprinting or other forms of DNA Amplification and/or DNA finger printing. The microfluidics chip may comprise two or more of any of these components (e.g., two sample receiving surfaces, three fluid distributors, etc.) In some configurations, one or more of these components may comprise the other. E.g., the transfer station can comprise a probe labelling station. In such a configuration, the one or more of these components would comprise the structure, programming, logic, design, and/or functionality of the component it comprises. E.g., if the detector comprises the probe labelling station, the detector would comprise the structure, programming, logic, design, and/or functionality to perform probe labeling.

As shown in FIG. 4, the microfluidics chip may comprise several components such as a tissue sample collector 50, a DNA extractor 51, a priming station 61, an electrophoresis station 54, a detector 57 (such as an autoradiography station, colorimetric station, fluorescent station, and chemiluminescent station), a fluid distributor 58, and a cleaning system 59. A tissue sample collector may comprise a container for storing tissue. The container may be configured to store human tissue such as blood, blood cells, epithelia cells, hair cells, saliva, or human tissue comprising DNA. The DNA extractor 51 may comprise equipment, chemicals, and software configured to extract DNA from human tissue. The DNA restriction digestion station 53 may comprise equipment, chemicals, and software configured to breakdown DNA strands into microsatellites. The electrophoresis station 54 may comprise equipment, chemicals, and software configured to separate microsatellites into bands of DNA based on band length. The transfer station 55 may comprise equipment, chemicals, and software configured to transfer the bands onto a membrane. The probe labelling station 56 may comprise equipment, chemicals, and software configured to bind probes that can be detected by autoradiography station. The probe labelling station 56 may comprise a probe wash station 46 configured to wash excess probes from the membrane. The detector 57 may be configured to detect positioning and location of probes. The detector may be configured to generate a dataset. The dataset may depict an image of the membrane showing the relative positions. The detector 57 may be configured to detect reflected light from the labelled primers bound to the bands. The detector may be configured to generate a first dataset. The first dataset may plot or show the frequency of light reflected and a relative position. The relative position may be based on the distance the STRs travelled during electrophoresis. As most cells from different individuals comprise unique strands of DNA (expect for clones and identical twins for example), the datasets will likely be unique for the same reason. The cleaning system 59 may be configured to clean or reset one or of these components. The priming station 61 may be configured to bind labelled STR primers with a polymerize chain reaction to the DNA sample to amplify the DNA fragments and form labelled STRs (short tandem repeats). A laser assembly or light source 351 may be configured to illuminate the bands of DNA with laser light of different frequencies.

The microfluidics chips of FIG. 4 may be configured to perform PCR fingerprinting or other forms of DNA Amplification and/or DNA finger printing. The microfluidics chip may comprise two or more of any of these parts (e.g., two sample receiving surfaces, three fluid distributors, etc.) In some configurations, one or more of these components may comprise the other. E.g., the transfer station can comprise a probe labelling station. In such a configuration, the one or more of these components would comprise the structure, programming, logic, design, and/or functionality of the component it comprises. E.g., if the detector comprises the probe labelling station, the detector would comprise the structure, programming, logic, design, and/or functionality to perform probe labeling.

The chip assembly may comprise additional components not listed above. A chip assembly may comprise components from FIG. 3 and FIG. 4. For example, a single chip assembly may comprise a laser assembly and a transfer station. Certain configurations of the invention may comprise more than one microfluidics chip.

Processor

Figure 5:
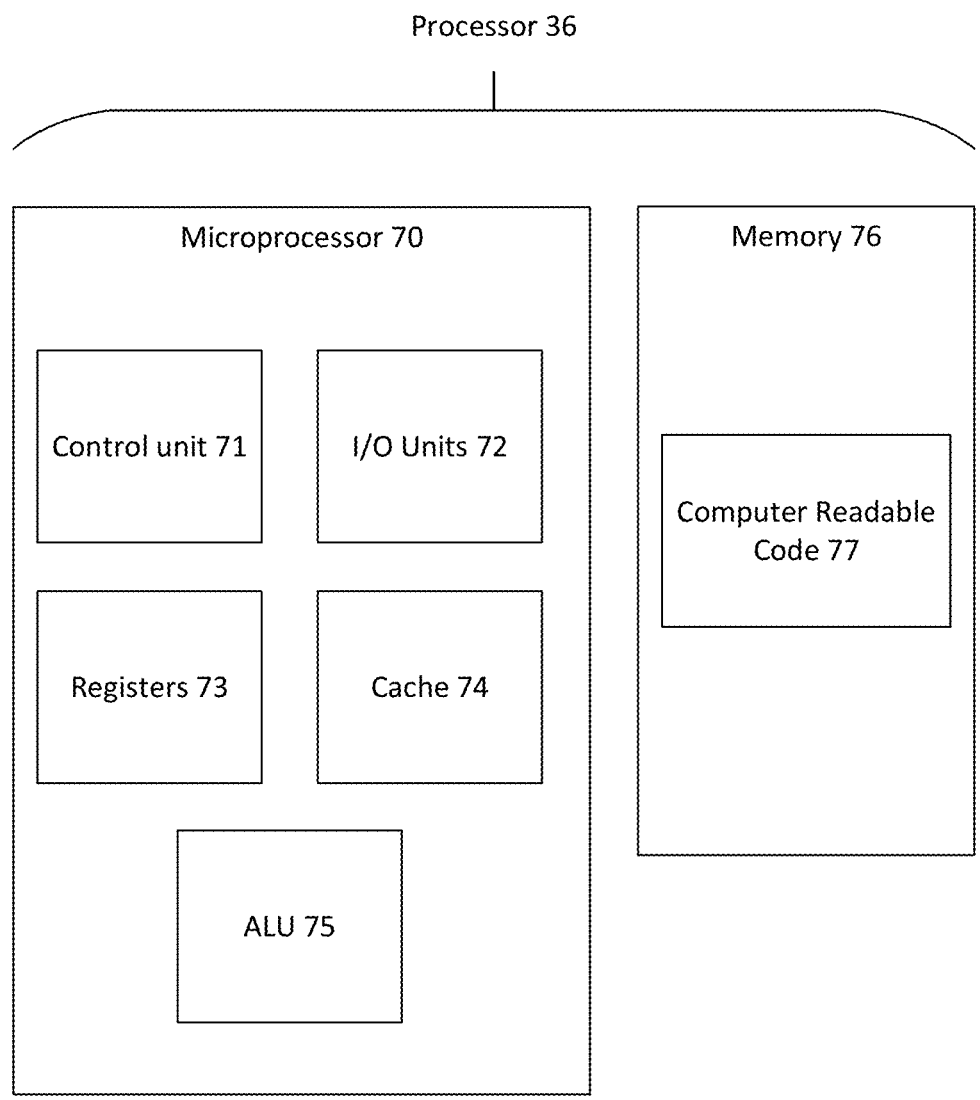
FIG. 5 shows an embodiment of a processor.

FIG. 5 shows a processor 36. The processor may comprise a microprocessor 70 and memory 76. The microprocessor may comprise a control unit 71, I/O units 72, arithmetic logic unit (ALU) 75, registers 73, and cache 74. The memory 76 may comprise tangible, non-transitory computer readable code 77 configured to cause the microprocessor to execute a sequence of instructions.

Access Control Process

Figure 6A:
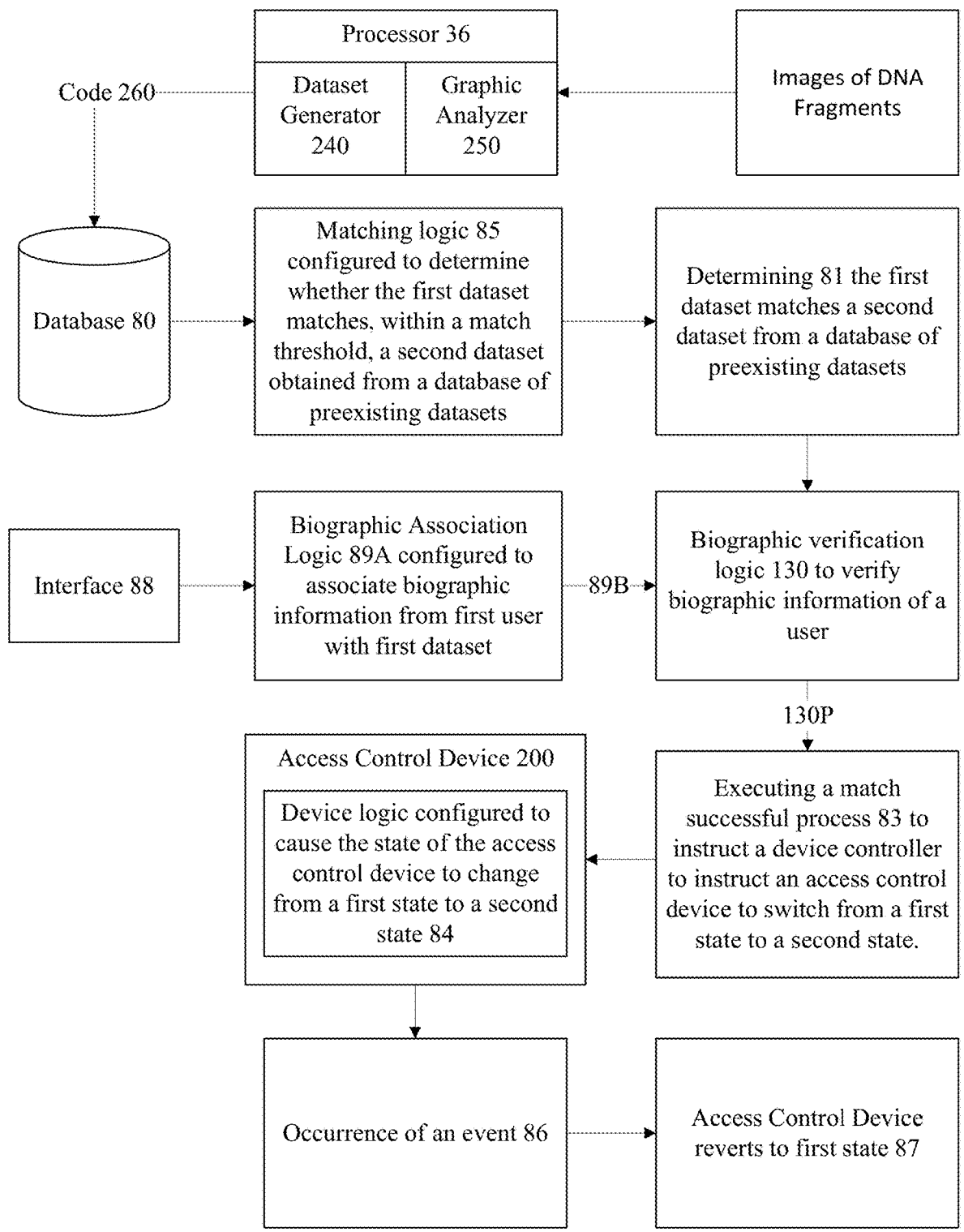
FIG. 6A illustrates an example of a match successful process.

FIG. 6A shows an example sequence of instructions that can be stored in the memory and executed by the processor in the DNA fingerprinting device and/or the database. In some configurations the database can comprise the processor. Or, the database may comprise its own processor (the database processor). The database may also comprise memory, a network interface, and non-transitory computer instructions for managing the database and/or executing some or all of the processes shown in FIG. 6A.

As shown, the processor 36 is configured to receive at least one image of DNA fragments from a user. The processor may transform the image into a first dataset (optionally using a dataset generator). The processor may send an instruction to the database to execute a matching logic 85 to determine whether the database contains a second dataset that matches the first dataset, optionally within a threshold value 81. The processor 36 may also request the user provide biographic information (name, address, phone number, etc.) through an interface 88 (such as keyboard). The processor may store this biographic information in the first dataset or associate 89B this biographic information with the first dataset. At a first time, a user may enter first biographic data or other first data through a first interface when transmitting the first biographic data or other first data to the processor or database processor. At a second time, the user may enter second biographic data or other second data through a second interface when transmitting the second biographic data or other second data to the processor or database processor. The first interface and second interface may be the same interface or different interfaces. The first biographic data or other first data may match, be the same, or not match the second biographic data or other second data.

The matching logic 85 may be configured to select specific portions of a dataset from which to run the comparison. The specific portions of the dataset may relate to a specific sequence of DNA in the current dataset to match a specific sequence of DNA in the previous dataset. The matching logic may be configured to select a number of portions of the dataset required for a positive match. Each portion may be associated with a specific DNA sequence.

A dataset generator 240 may be configured to generate a dataset from an image. For example, the dataset generator 240 may analyze intensity (Y-axis) vs frequency (X-axis) of an image depicting graph data. A graphic analyzer 250 may convert the dataset into alphanumeric string 260, hash, or code. The processor can store images, codes, graphs, hashes, etc. of the DNA fragments (bands) in the database 80. The processor may also be configured to use the matching logic 85 to request the database determine whether it contains a dataset that matches a specific pattern or other dataset. For example, the matching logic 85 may be configured to determine whether a first hash of a first image of DNA bands matches a second hash of a second image of DNA bands.

A dataset may be a representation of data having pairs of data points. For example, a dataset may display intensity and frequency. A dataset may comprise a chart or graph (e.g., having a displayed coordinate system), a table, the data in a data structure such as an array or linked list, it may be an image, or it may comprise a combination of charts, graphs, tables, reports, data, and images. A detector or the processor may be configured to generate an image or a dataset for the matching logic to compare against other datasets stored in a database.

The database may also comprise biographic information associated with or stored in the datasets. The database may comprise images of an autoradiograph, a colorimetric dataset, a fluorescent dataset, or a chemiluminescent dataset for example. A database may be an organized collection of structured information, or data, typically stored electronically in a computer or computer system. A database may be controlled by a database management system (DBMS). Together, the data and the DBMS, along with the applications that are associated with them, are referred to as a database system. Data with databases may be modeled in rows and columns in a series of tables to make processing and data querying efficient. Structured query language (SQL) may be used to write, query, and retrieve data. SQL is a programming language used by some relational databases to query, manipulate, and define data, and to provide access control. The database may take the form of a block-chain or relational database.

The processor and/or the database processor may comprise biographic association logic 89A configured to associate 89B biographic information from the user with an image or dataset. The processor and/or the database processor may comprise biographic verification logic 130 configured to verify whether biographic information associated with the second dataset matches 82 the first dataset, optionally within a threshold value. The processor or database processor may execute a match successful process 83. The match successful process may program or a device controller (in the processor or database processor) to instruct a device logic 210 in the access control device 200 to take an action. The action may be to switch from a first state to a second state 87. The access control device 200 may be an electronic gate or an electronic lock. The access control device may also be a computer comprising access control software. The computer may comprise its own processor, memory, and non-transitory computer readable code to cause the computer to process a sequence of instructions. Although FIG. 6A shows the biographic verification process occurring after the matching logic determines a dataset match, in some configurations the biographic verification process may occur first. The process of the matching logic determining whether or not there is a dataset match is an example of a biometric verification process. The datasets in this example contain biometric information or a representation of biometric information.

The access control device 200 may comprise an access control device processor (ACDP) which may comprise logic in the form of tangible, non-transitory computer readable code configured to cause the ACDP to perform certain functions. The ACDP may comprise device logic 210 configured to cause a state of the access control device 200 to change from a first state to a second state. ACDP may comprise other instructions and circuits found in a processor.

Device Logic

Figure 6B:
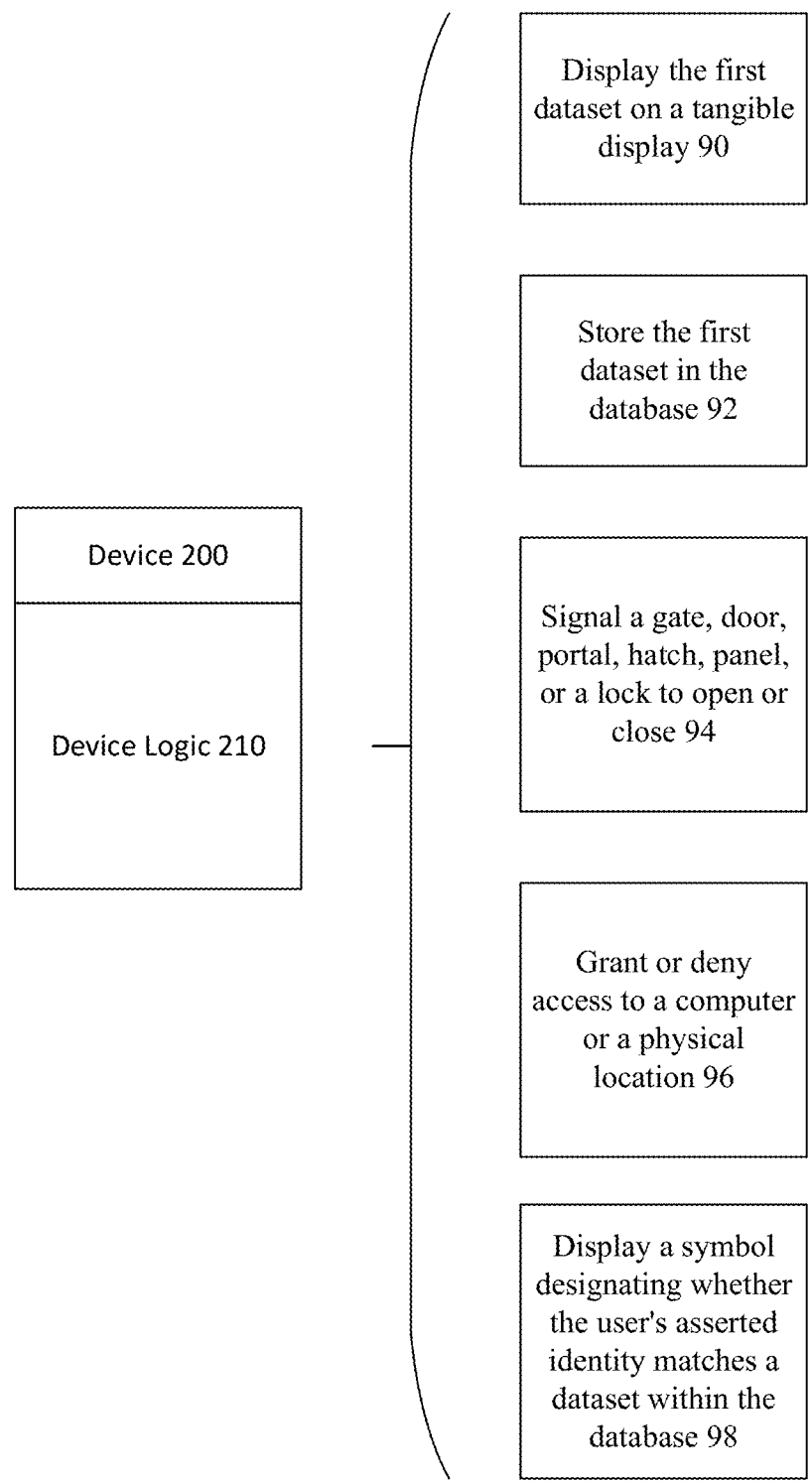
FIG. 6B illustrates an example of device logic.
Figure 6C:
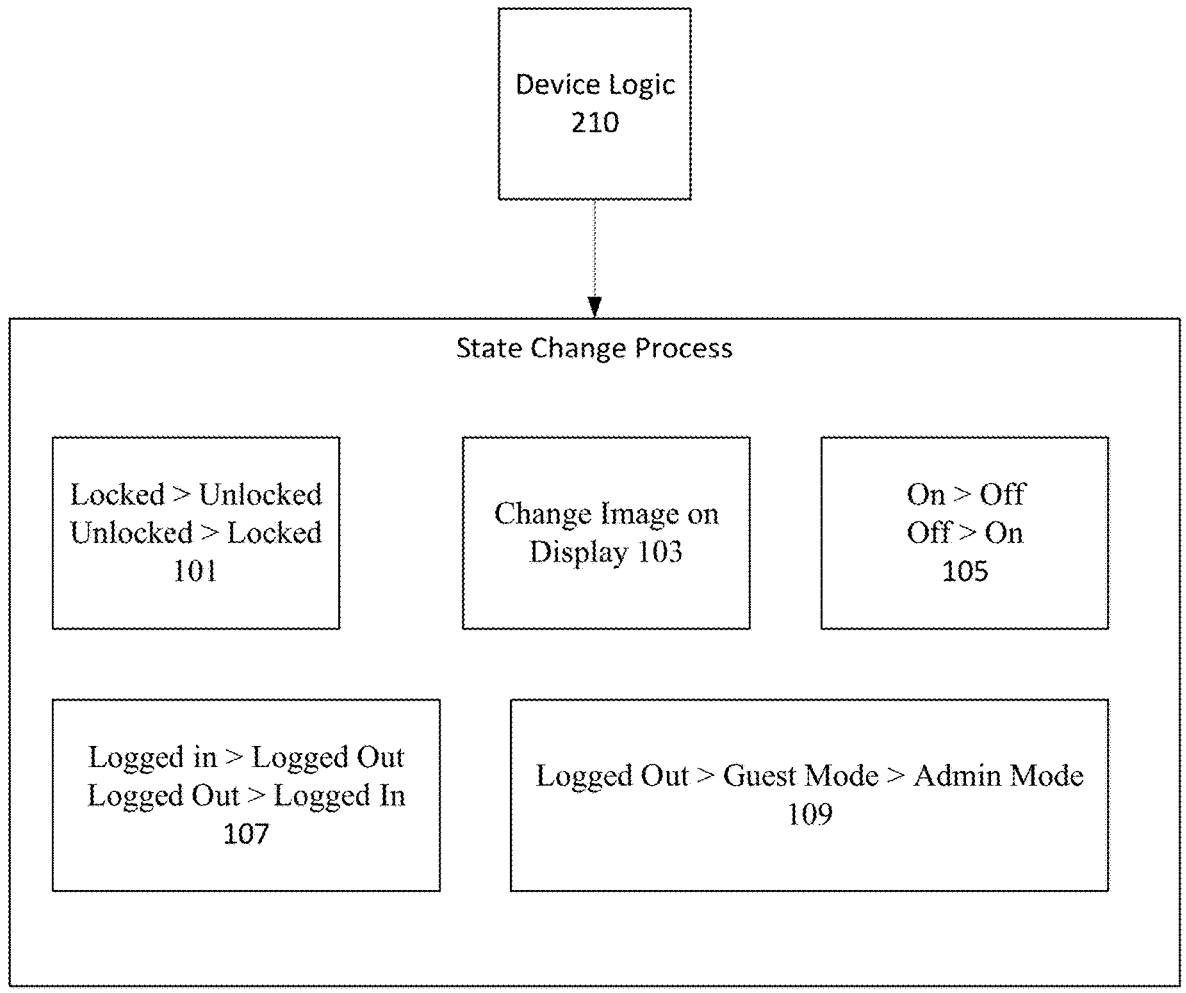
FIG. 6C shows another view of device logic.

FIGS. 6B and 6C illustrate an example of the device logic. For example, the match successful process may be configured to cause a state of an access control device to change from a first state to a second state. For example, the match successful process may comprise and/or the access control device may be configured to display 90 the first dataset on a tangible display; store 92 the first dataset in the database; signal 94 a gate, door, portal, hatch, panel, or a lock to open or close; grant or deny access 96 to a computer or a physical location; or display 98 a symbol designating whether the user's asserted identity matches a dataset within the database.

FIG. 6C shows examples of the state change process 100. The change state process may switch the device from locked to unlocked or unlocked to locked 101; change an image or text on a display 103; turn a device off or on 105; log a user into the device or log the user out of the device 107; switch the device between logged out, guest mode, or admin mode 109.

Access Control Panel

Figure 6D:
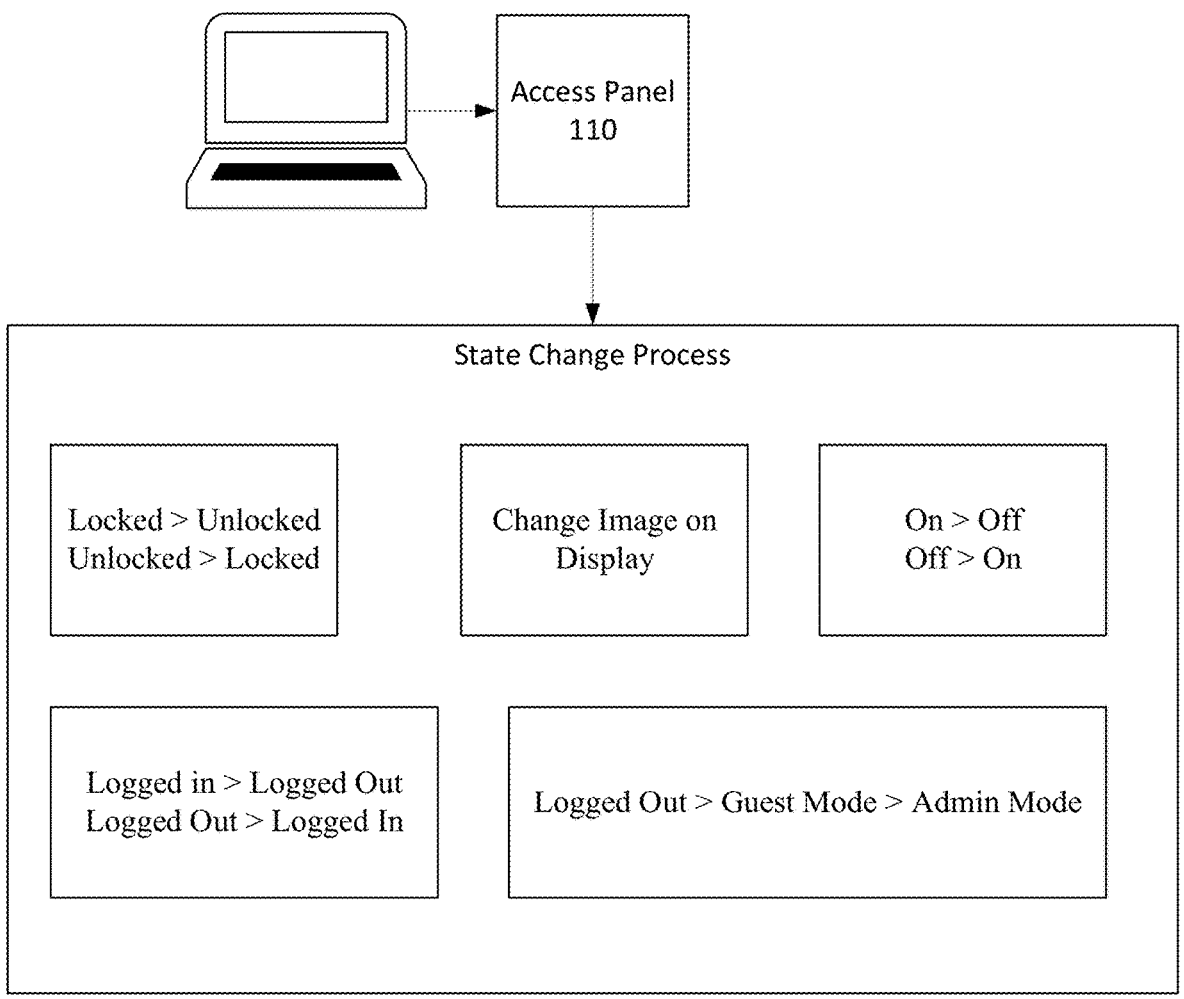
FIG. 6D shows an access control panel comprising a DNA fingerprinting device configured to control a laptop.

FIG. 6D shows an access control panel 110 comprising a DNA fingerprinting device configured to control a device such as a laptop or computer. The access control panel may be configured to be configured to perform the change state process just described. When a user wants to, for example, lock the device, the user may use the access control panel to configure the device to lock. Similarly, the user may use the access control panel to turn a display on or log into the device. A first state of a display comprise displaying a blank image and a second state of a display may be displaying a first dataset. A computer may have a locked and unlocked state. The computer may also have a logged-in and logged out state. Devices may have more than two states. The match successful process and/or device logic may be configured to cause a device to transition between three or more states or modes. For example, a computer can be in a locked mode. The computer may have a guest mode/state, admin mode/state, and a user mode/state.

Figure 6E:
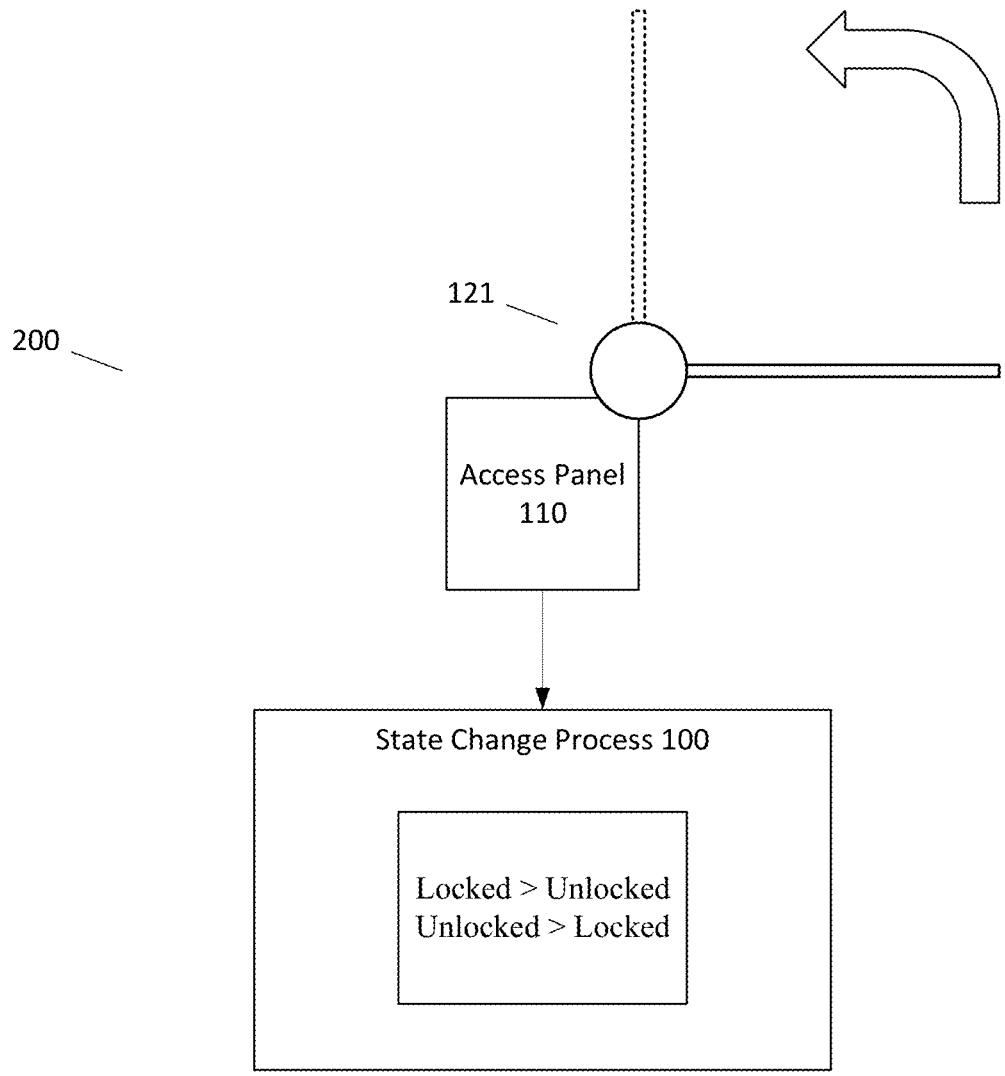
FIG. 6E shows an access control panel integrated into an electronic gate; the access panel comprising a DNA fingerprinting device configured to control or cause the electronic gate change from a first state to a second state (e.g., closed to opened).

FIG. 6E shows an access control panel comprising a DNA fingerprinting device configured to control a cause an electronic gate 121 change from a first state to a second state (the state change process 100). In this example, the access control device 200 device may comprise an electronic gate 121. The electronic gate may comprise a lock. In further example, a first state may be a locked state and a second state may be an unlocked state.

Biographic Authentication Process & Biographic Authentication Logic

Figure 7:
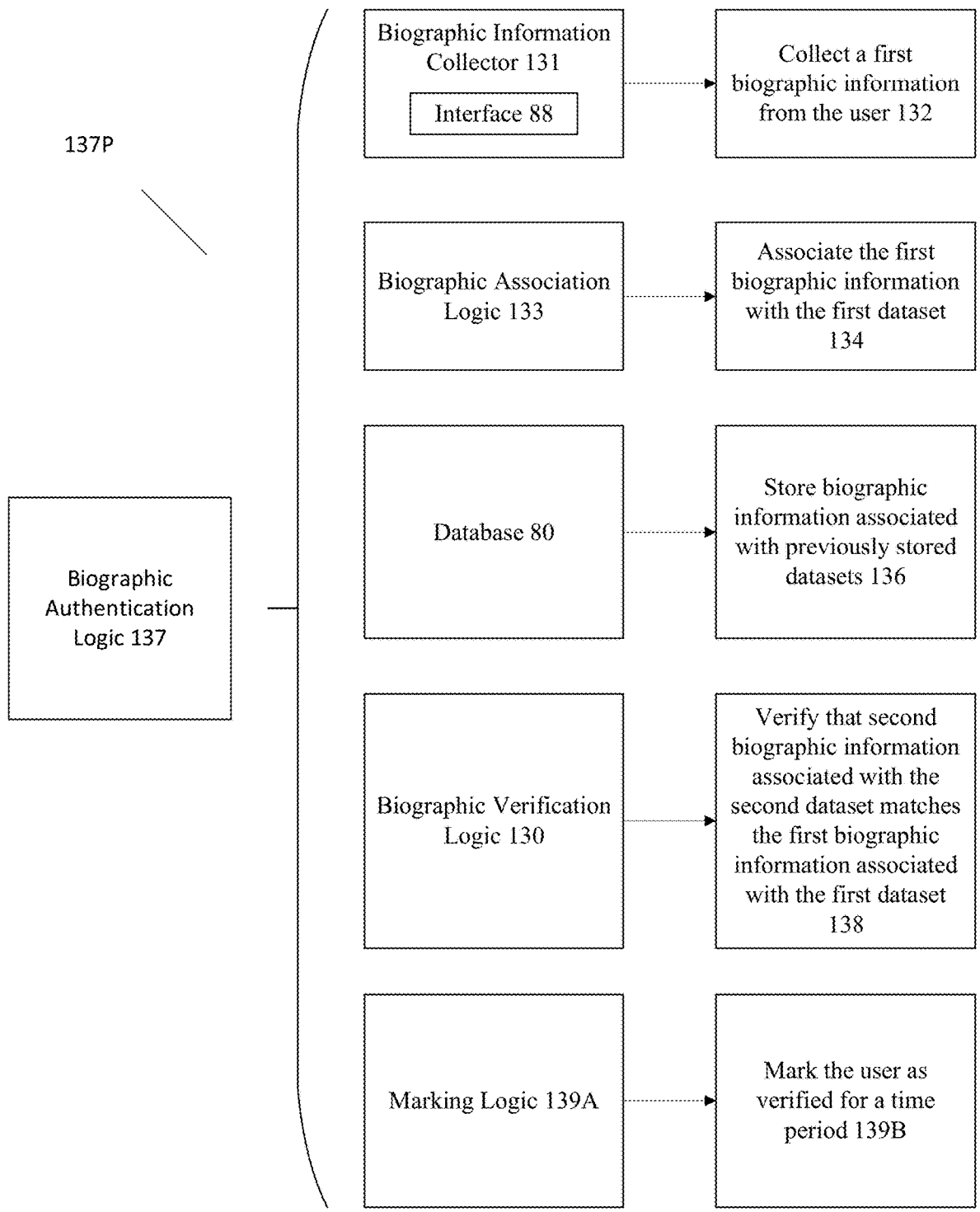
FIG. 7 shows an example of a biographic authentication process.

FIG. 7 shows an example of a biographic authentication process 137P and a biographic authentication logic 137. The biographic authentication logic 137 may comprise or be connected to a biographic information collector 131, a biographic association logic 133, a database 80, biographic verification logic 130, and a marking logic 139A. The biographic information collector 131 may be configured to collect a first biographic information from the user 132 through an interface 88. The biographic association logic 133 may be configured to associate the first biographic information with the first dataset 134. The database 80 may be configured to store biographic information associated with a stored dataset 136. The biographic verification logic 130 may be configured to verify 130P that second biographic information associated with the second dataset matches the first biographic information associated with the first dataset 138. The marking logic 139A may be configured for marking 139B the user as verified for a time period. The time period may be a range of times such as 1-20 seconds, 1-5 minutes, 10-20 minutes, 1-2 hours, 2-3 days, 1-4 weeks, etc.

RFLP Based Fingerprinting Authentication Process

Figure 8A:
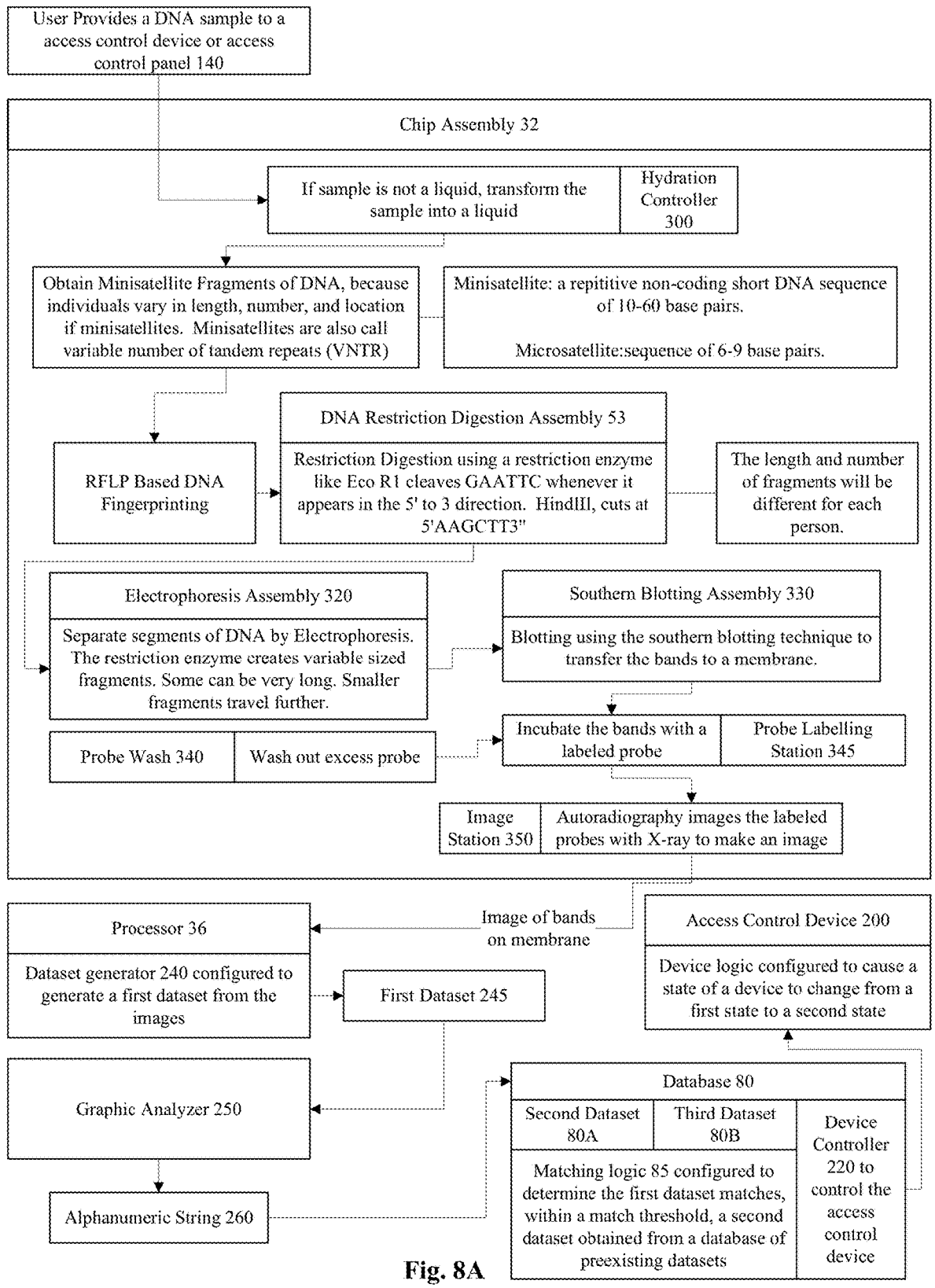
FIG. 8A shows an example process flow of RFLP based DNA fingerprinting that the microfluidic chip of FIG. 3 may perform.

FIG. 8A shows an example process of authenticating a user. The process involves providing a DNA sample 140 to a chip assembly 32. An access control panel may comprise the chip assembly 32 and a processor 36. The access control panel 120 may be connected to an access control device 200.

The chip assembly may comprise a hydration controller 300 configured to transform the DNA sample into a liquid. The chip assembly may comprise a DNA restriction digestion station 53 configured to generate minisatellite fragments of DNA. Minisatellite fragments of DNA vary in individuals in length, number, and location. Minisatellites are also known as variable number of tandem repeats. A minisatellite may be a repetitive, non-coding short DNA sequences of 10-60 base pairs. Microsatellites are generally a sequence of 6-9 base pairs. System that perform restriction digestion for DNA fingerprinting are known as RFLP based DNA fingerprinting. The chip assembly may comprise an electrophoresis assembly 320 containing a gel with pores (like agarose gel). In electrophoresis, an electric current causes smaller length fragments to travel further in the gel than longer length fragments in a set time period. Through electrophoresis, the electrophoresis assembly can separate the minisatellite fragments by their lengths. A southern blotting assembly 330 may be configured to use the southern blotting technique to transfer the DNA fragments to a membrane. A probe labelling station 56 may add probes (such as radioactive probes) to the fragments in the membrane. A probe wash 340 may wash out or remove any excess probes. An imaging station 350 may generate autoradiographic images of the labelled probes to create an image of the fragments on the membrane. The imaging station may transfer the image to the processor 36.

The processor 36 may be configured to receive the first image of the user's DNA. The processor 36 may comprise a dataset generator 240 to generate a first dataset 245 from the image. The dataset generator 240 may be invoke a graphic analyzer 250 configured to generate a mathematical representation of the fragments in the image to facilitate matching comparison (for example an alphanumeric string 260 that represents digital image as a code of numbers and letter). For example, the graphics analyzer 250 may determine how many DNA fragments are in the image, label each of the fragments, and/or determine an actual length and/or relative length of DNA fragments in the image.

The database 80 may comprise a plurality of datasets such as a second dataset 80A and third datasets 80B. A dataset may take the form of an alphanumeric strings representing the digital images of other users imaged DNA. A dataset may also be the image of the DNA fragments as well. The database may sort the alphanumeric strings or codes. The database may be configured to execute various database commands such as sort, get, save, etc. In some configurations, the processor can simply request the database return a value of true if it contains a code associated with the first dataset, and a value of false if it does not. In other configurations, the database may comprise matching logic configured to compare a first dataset received by the processor against other datasets in the database to determine whether there is a match within a threshold.

The database processor or the processor in the DNA fingerprinting device or both may comprise a matching logic 85. The matching logic may be configured to perform a match operation comparing a first dataset, first image, first biometric data, first biographic data, first metadata or combination thereof (collectively "the first data") with a second dataset, second image, second biometric data, second biographic data, second metadata, or combination thereof (collectively "the second data"). The second data may be stored in a database. The matching logic may perform multiple match operations against datasets, images, biometric data, biographic data, metadata, or combinations thereof (collectively "stored data") stored in the database. The matching logic may be configured to identify a single dataset, single image, single biometric data, single biographic data, single metadata, or single combination thereof (collectively a "single data) in the database that has a highest similarity value as compared to the first data. The matching logic 85 may be configured to determine a first data matches a second data if the similarity value is above a threshold value. The threshold value may be set by the user, may have a default value, etc. A machine learning process may be used to algorithmically determine the threshold value.

A matching logic 85 may be configured to compare the first dataset against one or more datasets in the database. The matching logic 85 may be configured to determine a match based on a first data and a second data. Determining a match means the matching logic has computed that there is at least some similarity between the first data and the second data. A match may be a partial patch, regular expression match, fuzzy match, exact match, pattern match, partial pattern match, etc. Matching may include determining whether a pair of images or datasets exactly matches, fuzzy matches, threshold matches, pattern matches, partial pattern matches, etc. The matching logic may be configured to compare biographic data, biometric data, metadata, identifiers, a hash of biometric data, coded data, or other information in the dataset when determining a match. Determining a match may comprise a single match operation or multiple match operations.

The matching logic may be configured to send a first instruction to an access control device if a match is found. The matching logic may be configured to send a second instruction to the access control device if no match is found. The matching logic 85 may use fuzzy matching or threshold matching to identify a match within a certain threshold of error.

The access control device 200 may switch from a first position to a second position or switch from a first state to a second state when it receives the first instruction. The access control device 200 may switch from the second position to the first position or switch from the second state to a first state when it receives the second instruction.

Referring to FIG. 6A, the access control device may have a default position or default state. In such configurations, the access control device may switch from the default position or state to a second position or second state upon receipt of the first instruction. The access control device may revert back 87 to the default position or default state after an occurrence of an event 86. Example events include: passage a specific amount of time 10 seconds, 20 seconds, 1 minute, 5 minutes, 1 hour, 1 day, etc., one or more objects pass through a sensor (e.g. a person walks through an electronic gate), an object or person is no longer detected within a preset radius of a sensor (e.g., a Bluetooth device is no longer within range of Bluetooth sensor); a user no longer interacts with the device for a set period of time (e.g., a laptop logs out after a person stopped using the laptop for more than 15 minutes), etc.

PCR Based Fingerprinting Authentication Process

Figure 8B:
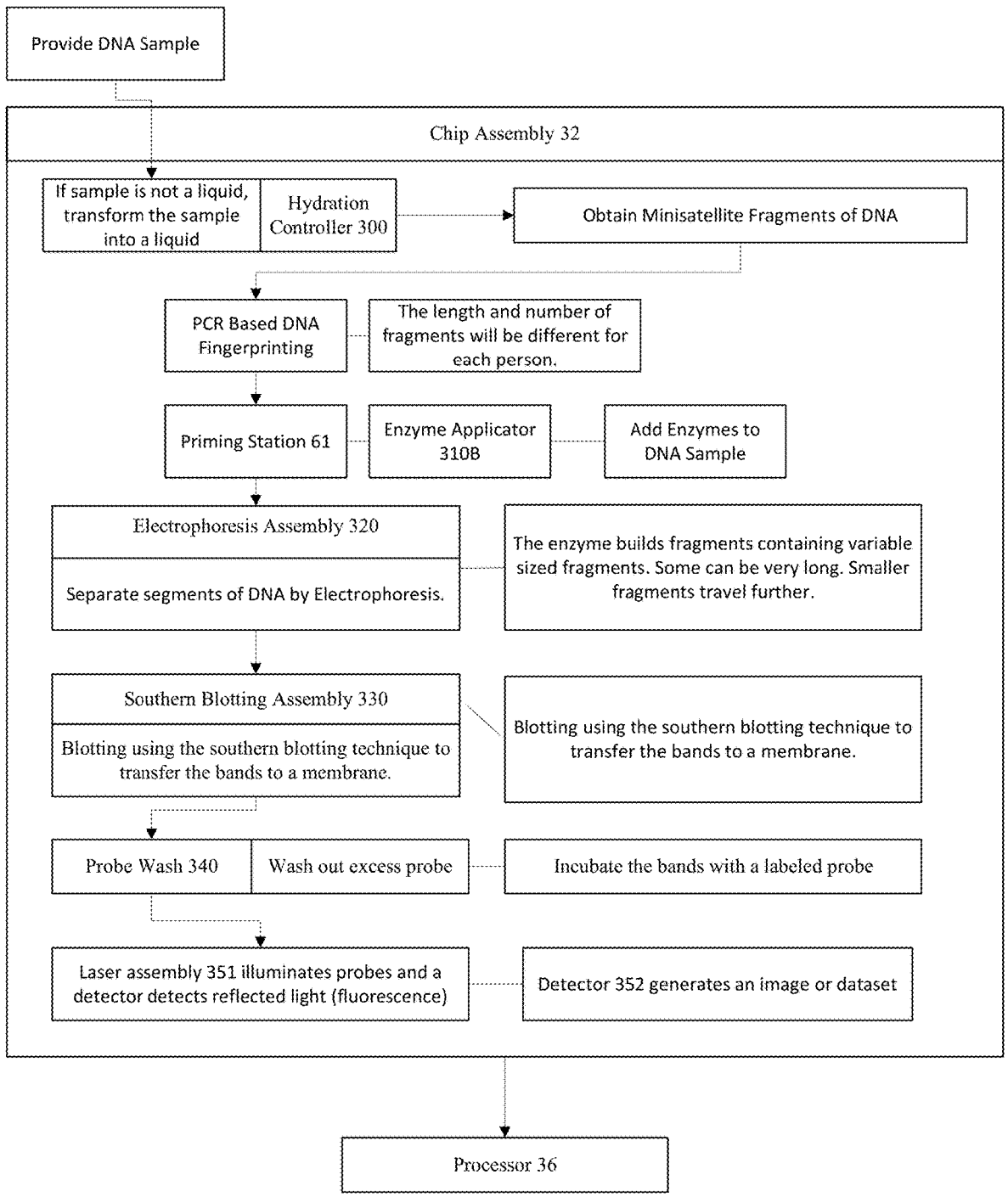
FIG. 8B shows an example process flow of PCR based DNA fingerprinting that the microfluidic chip of FIG. 4 may perform.

FIG. 8B shows an example process of authenticating a user. The process involves providing a DNA sample 140 to a chip assembly 32. An access control panel may comprise the chip assembly 32 and a processor 36. The access control panel 120 may be connected to an access control device 200.

The chip assembly may comprise a hydration controller 300 configured to transform the DNA sample into a liquid. The chip assembly may comprise a priming station 61 configured to bind labelled STR primers with a (PCR) polymerize chain reaction to the DNA sample to amplify DNA fragments and form labelled STRs (short tandem repeats). The chip assembly may comprise an enzyme applicator 310B configured to generate minisatellite fragments of DNA. Systems that perform generate DNA fragments through enzymatic reactions may be referred to as PCR based DNA fingerprinting. The chip assembly may comprise an electrophoresis assembly 320 containing a gel with pores (like agarose gel). In electrophoresis, an electric current causes smaller length fragments to travel further in the gel than longer length fragments in a set time period. Through electrophoresis, the electrophoresis assembly can separate the minisatellite fragments by their lengths. A southern blotting assembly 330 may be configured to use the southern blotting technique to transfer the DNA fragments to a membrane. A probe labelling station 345 may add probes (such as radioactive probes) to the fragments in the membrane. A probe wash 340 may be wash out or remove any excess probes. A laser assembly or light source 351 may illuminate probes. A detector 352 may detect light reflected by the probes. The detector may generate an image or dataset. The detector may transfer the image to the processor 36. Once the processor 36 receives the image or dataset, process may continue as set forth in FIG. 8B.

While FIGS. 8A and 8B illustrate autoradiography and fluorescence respectively, other methods may be used such as colorimetric and chemiluminescent detection. Additionally, other methods of extracting DNA from a sample (e.g., other than RFLP and PCR) may be used.

Figure 9:
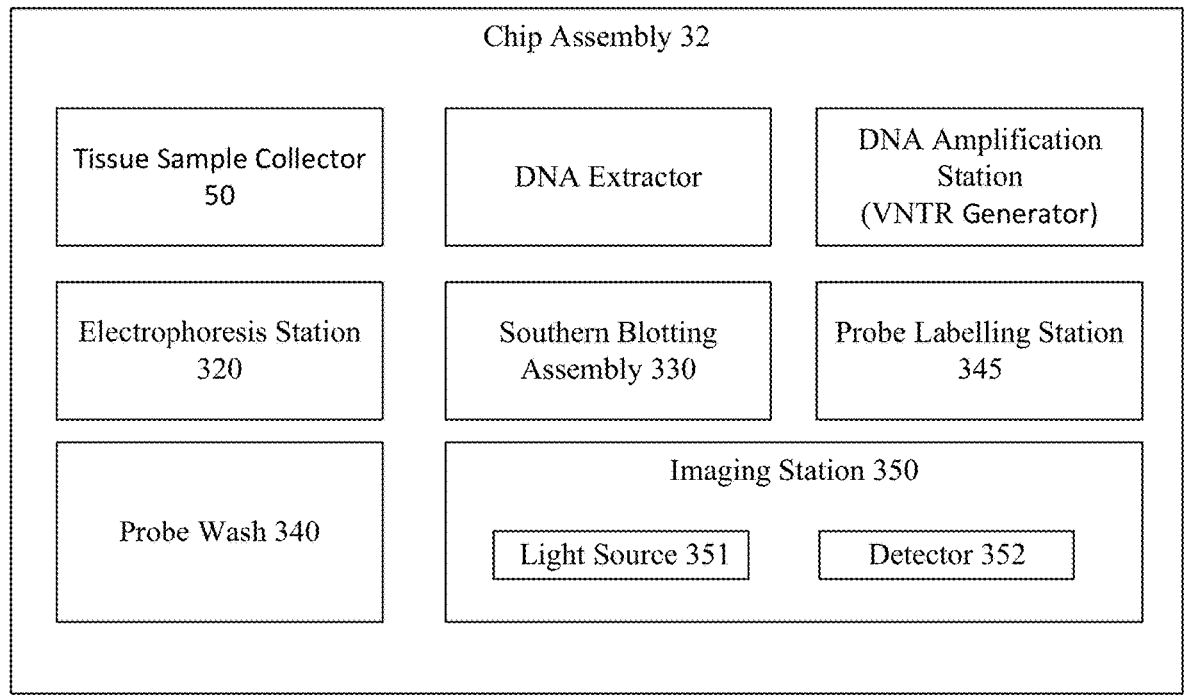
FIG. 9 shows a configuration of the chip assembly and the processor.
Figure 9:
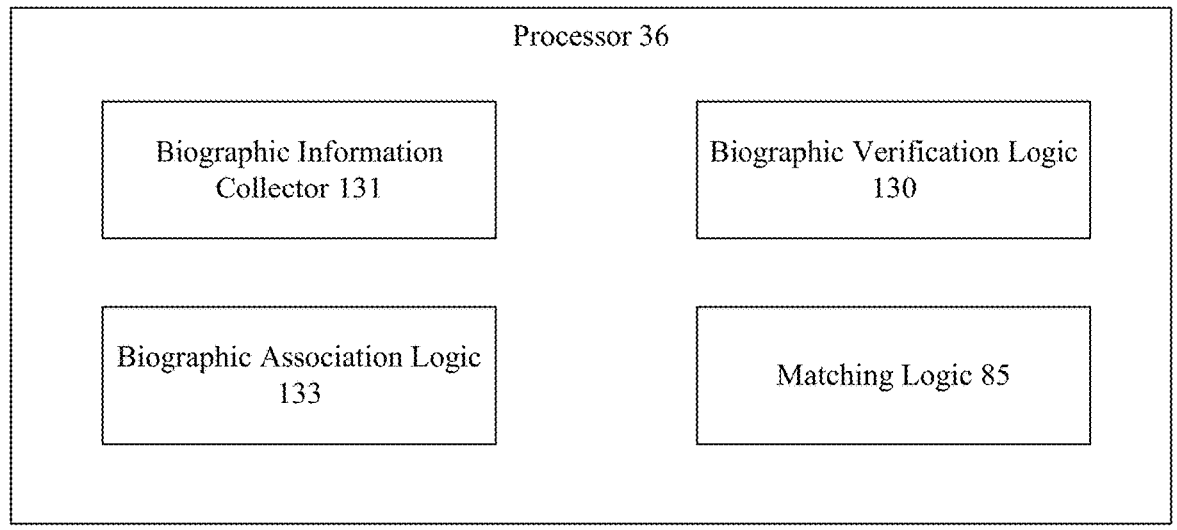

FIG. 9 illustrates a schematic view of some exemplary components of the DNA fingerprinting device comprising a chip assembly 32 and the processor 36. The chip assembly may comprise a tissue sample collector 50 for collecting a sample of tissue, a DNA extractor 51 for extracting DNA from a tissue sample, a DNA amplification station for generating VNTR, an electrophoresis assembly 320, a Southern blotting assembly 330, a probe labelling station 345, a probe wash 340, and an imaging station 350. The processor 36 may comprise a biographic information collector 131, a biographic association logic 133, biographic verification logic 130, and matching logic 85. The matching logic 85 may perform a comparison algorithm against biometric information such as DNA fragments.

CONCLUSION

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

For instances in which the systems and/or methods discussed here may collect personal information about users, or may make use of personal information, the users may be provided with an opportunity to control whether programs or features collect personal information, e.g., information about a user's social network, social actions or activities, profession, preferences, or current location, or to control whether and/or how the system and/or methods can perform operations more relevant to the user. In addition, certain data may be anonymized in one or more ways before it is stored or used, so that personally identifiable information is removed. For example, a user's identity may be anonymized so that no personally identifiable information can be determined for the user, or a user's geographic location may be generalized where location information is obtained, such as to a city, ZIP code, or state level, so that a particular location of a user cannot be determined. Thus, the user may have control over how information is collected about him or her and used.

Embodiments may be implemented as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "data processing system" encompasses all apparatus, devices, and machines for processing data, including by way of example a programmable processor, a computer, or multiple processors or computers. The system may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

Embodiments and functional operations described in this specification may be implemented in digital electronic circuitry, or in computer software, firmware, or hardware, including the structures disclosed in this specification and their structural equivalents, or in combinations of one or more of them. For example, elements designated as engines, generators, identifiers, tools, analyzers, calculators, classifiers, checkers, finders, logic recorders, visualizers, aggregators, modules, nodes, managers, organizers, algorithms, etc. may be implemented in a variety of ways. A computer program (also known as a program, software, software application, script, or code) may be written in any form of programming language, including compiled or interpreted languages, and it may be deployed in any form, including as a standalone program or as a module, component, subroutine, or other unit suitable for use in a computing environment.

A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both.

The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide interaction with a user, embodiments may be implemented on a computer having a display device, like a TV or monitor (CRT or LCD, etc.) for displaying information to the user. Computers may have peripherals like a keyboard, trackpad, mouse, etc. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

Embodiments may be implemented in a computing system that includes a back end component, e.g., as a data server, or that includes a middleware component, e.g., an application server, or that includes a front end component, e.g., a client computer having a graphical user interface or a web browser through which a user may interact with an implementation, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

The computer and/or computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Thus, particular embodiments have been described. Other embodiments are within the scope of the following claims. For example, the actions recited in the claims may be performed in a different order and still achieve desirable results.

Computer System

The invention may include or be connected to a computer comprising a hardware processor communicatively coupled to an instruction memory and to a data memory. The instruction memory can be configured to store, on at least a non-transitory computer-readable storage medium as described in greater detail below, executable program code. The hardware processor may include multiple hardware processors and/or multiple processor cores. The hardware processor may include hardware processors from different devices that cooperate. The computer system may execute one or more basic instructions included in the memory executable program code in instruction memory.

Relationship Between Hardware Processor and Executable Program Code

The relationship between the executable program code in the instruction memory and the hardware processor is structural; the executable program code is provided to the hardware processor by imparting various voltages at certain times across certain electrical connections, in accordance with binary values in the executable program code, to cause the hardware processor to perform some action, as now explained in more detail.

A hardware processor may be thought of as a complex electrical circuit that is configured to perform a predefined set of basic operations in response to receiving a corresponding basic instruction selected from a predefined native instruction set of codes.

The predefined native instruction set of codes is specific to the hardware processor; the design of the processor defines the collection of basic instructions to which the processor will respond, and this collection forms the predefined native instruction set of codes.

A basic instruction may be represented numerically as a series of binary values, in which case it may be referred to as a machine code. The series of binary values may be represented electrically, as inputs to the hardware processor, via electrical connections, using voltages that represent either a binary zero or a binary one. These voltages are interpreted as such by the hardware processor.

Executable program code may therefore be understood to be a set of machine codes selected from the predefined native instruction set of codes. A given set of machine codes may be understood, generally, to constitute a module. A set of one or more modules may be understood to constitute an application program or "app." An app may interact with the hardware processor directly or indirectly via an operating system. An app may be part of an operating system.

Computer Program Product

A computer program product is an article of manufacture that has a computer-readable medium with executable program code that is adapted to enable a processing system to perform various operations and actions. Stated differently, the executable program code can embody or functionality of instructions that cause a computer, e.g., that cause the processor, to perform particular operations or processes.

A computer-readable medium may be transitory or non-transitory. A transitory computer-readable medium may be thought of as a conduit by which executable program code may be provided to a computer system, a short-term storage that may not use the data it holds other than to pass it on.

The buffers of transmitters and receivers that briefly store only portions of executable program code when being downloaded over the Internet is one example of a transitory computer-readable medium. A carrier signal or radio frequency signal, in transit, that conveys portions of executable program code over the air or through cabling such as fiber-optic cabling provides another example of a transitory computer-readable medium. Transitory computer-readable media convey parts of executable program code on the move, typically holding it long enough to just pass it on.

Non-transitory computer-readable media may be understood as a storage for the executable program code. Whereas a transitory computer-readable medium holds executable program code on the move, a non-transitory computer-readable medium is meant to hold executable program code at rest. Non-transitory computer-readable media may hold the software in its entirety, and for longer duration, compared to transitory computer-readable media that holds only a portion of the software and for a relatively short time. The term, "non-transitory computer-readable medium," specifically excludes communication signals such as radio frequency signals in transit.

The following forms of storage exemplify non-transitory computer-readable media: removable storage such as a universal serial bus (USB) disk, a USB stick, a flash disk, a flash drive, a thumb drive, an external solid-state storage device (SSD), a compact flash card, a secure digital (SD) card, a diskette, a tape, a compact disc, an optical disc; secondary storage such as an internal hard drive, an internal SSD, internal flash memory, internal non-volatile memory, internal dynamic random-access memory (DRAM), read-only memory (ROM), random-access memory (RAM), and the like; and the primary storage of a computer system.

Different terms may be used to express the relationship between executable program code and non-transitory computer-readable media. Executable program code may be written on a disc, embodied in an application-specific integrated circuit, stored in a memory chip, or loaded in a cache memory, for example. Herein, the executable program code may be said, generally, to be "in" or "on" a computer-readable media. Conversely, the computer-readable media may be said to store, to include, to hold, or to have the executable program code.

Creation of Executable Program Code

Software source code may be understood to be a human-readable, high-level representation of logical operations. Statements written in the C programming language provide an example of software source code.

Software source code, while sometimes colloquially described as a program or as code, is different from executable program code. Software source code may be processed, through compilation for example, to yield executable program code. The process that yields the executable program code varies with the hardware processor; software source code meant to yield executable program code to run on one hardware processor made by one manufacturer, for example, will be processed differently than for another hardware processor made by another manufacturer.

The process of transforming software source code into executable program code is known to those familiar with this technical field as compilation or interpretation and is not the subject of this application.

User Interface

A computer system may include a user interface controller under control of the processing system that displays a user interface in accordance with a user interface module, i.e., a set of machine codes stored in the memory and selected from the predefined native instruction set of codes of the hardware processor, adapted to operate with the user interface controller to implement a user interface on a display device. Examples of a display device include a television, a projector, a computer display, a laptop display, a tablet display, a smartphone display, a smart television display, or the like.

The user interface may facilitate the collection of inputs from a user. The user interface may be graphical user interface with one or more user interface objects such as display objects and user activatable objects. The user interface may also have a touch interface that detects input when a user touches a display device.

A display object of a user interface may display information to the user. A user activatable object may allow the user to take some action. A display object and a user activatable object may be separate, collocated, overlapping, or nested one within another. Examples of display objects include lines, borders, text, images, or the like. Examples of user activatable objects include menus, buttons, toolbars, input boxes, widgets, and the like.

Communications

The various networks are illustrated throughout the drawings and described in other locations throughout this disclosure, can comprise any suitable type of network such as the Internet or a wide variety of other types of networks and combinations thereof. For example, the network may include a wide area network (WAN), a local area network (LAN), a wireless network, an intranet, the Internet, a combination thereof, and so on. Further, although a single network is shown, a network can be configured to include multiple networks.

Considerations

For any computer-implemented embodiment, "means plus function" elements will use the term "means;" the terms "logic" and "module" have the meaning ascribed to them above and are not to be construed as generic "means." An interpretation under 35 U.S.C. § 112 (f) is desired only where this description and/or the claims use specific terminology historically recognized to invoke the benefit of interpretation, such as "means," or "means for" and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not to be taken as limiting or restricting the systems, techniques, approaches, methods, or devices to those appearing in any section. Rather, the teachings and disclosures herein can be combined or rearranged with other portions of this disclosure and the knowledge of one of ordinary skill in the art. It is intended that this disclosure encompass and include such variation.

The indication of any elements or steps as "optional" does not indicate that all other or any other elements or steps are mandatory. The claims define the invention and form part of the specification. Limitations from the written description are not to be read into the claims.

Certain attributes, functions, steps of methods, or sub-steps of methods described herein may be associated with physical structures or components, such as a module of a physical device that, in implementations in accordance with this disclosure, make use of instructions (e.g., computer executable instructions) that may be embodied in hardware, such as an application specific integrated circuit, or that may cause a computer (e.g., a general-purpose computer) executing the instructions to have defined characteristics. There may be a combination of hardware and software such as processor implementing firmware, software, and so forth so as to function as a special purpose computer with the ascribed characteristics. For example, in embodiments a module may comprise a functional hardware unit (such as a self-contained hardware or software or a combination thereof) designed to interface the other components of a system such as through use of an application programming interface (API). In embodiments, a module is structured to perform a function or set of functions, such as in accordance with a described algorithm. This disclosure may use nomenclature that associates a component or module with a function, purpose, step, or sub-step to identify the corresponding structure which, in instances, includes hardware and/or software that function for a specific purpose. For any computer-implemented embodiment, "means plus function" elements will use the term "means;" the terms "logic" and "module" and the like have the meaning ascribed to them above, if any, and are not to be construed as means.

While certain implementations have been described, these implementations have been presented by way of example only and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure.

The invention claimed is:

1. A method of controlling access to a secure device or location comprising:
   collecting a tissue sample from a user with a tissue sample collector;
   providing the tissue sample to a chip assembly comprising a DNA extractor;
   extracting DNA from the tissue sample using a DNA extraction technique;
   performing electrophoresis in a microfluidics chip to create bands of DNA fragments with an electrophoresis station;
   binding probes to the DNA fragments with a probe labelling station;
   an imaging station generate a first image of DNA bands;
   a processor determining the first image matches a second image previously stored in a database;
   the processor instructing a device controller to send a signal to a device logic; and
   the device logic instructing an access control device to switch from a first state to a second state.

2. The method of claim 1 comprising transferring the DNA bands to a membrane in the microfluidics chip using southern blotting technique.

3. The method of claim 1 wherein the processor determines whether the first image matches a second image within a threshold value.

4. The method of claim 1 comprising performing RFLP-based (restriction fragment length polymorphism) DNA fingerprinting by performing restriction digestion using restriction enzymes with a restriction digestion station.

5. The method of claim 1 comprising autoradiographing the DNA bands and probes to generate a first autoradiograph of the DNA bands with the imaging station.

6. The method of claim 1 comprising binding labelled STR primers with a polymerize chain reaction to amplify DNA fragments and form labelled STRs (short tandem repeats) with a priming station.

7. The method of claim 1 comprising fluorescing the bands with the imaging station.

8. The method of claim 7 comprising detecting reflected light from the labelled primers bound to the bands with a detector.

9. The method of claim 8 comprising the detector generating a first dataset; the first dataset showing a frequency of light reflected and a relative position; the relative position based on a distance the STRs travelled during electrophoresis.

10. The method of claim 1 wherein the imaging station comprises an autoradiography station.

11. The method of claim 1 comprising:
    a wash station cleaning components of the chip assembly; and
    a power source providing electricity to the chip assembly and processor in the DNA fingerprinting device.

12. The method of claim 1 wherein the device logic causes the access control device to:
    open or close a barrier;
    grant or deny access to a computer or a physical location; or
    display a symbol designating whether the user's asserted identity matches a dataset within the database.

13. The method of claim 1 comprising:
    a biographic information collector collecting a first biographic information from the user;
    the user having a name and phone number; the biographic information comprising the user's name and user's phone number;
    a biographic association logic associating the first biographic information with the first image;
    the database storing biographic information associated with previously stored images; and
    a biographic verification logic verifying that second biographic information associated with the second image matches the first biographic information associated with the first image; and
    a marking logic marking the user as verified for a time period.

14. An access control system comprising:
    a chip assembly for DNA fingerprinting comprising:
        a tissue sample collector configured to collect a tissue sample containing cells containing DNA from a user;
        the tissue sample collector providing the tissue sample to a DNA extractor;
        the DNA extractor configured to extract DNA from the cells;
        an electrophoresis station configured to create bands of DNA fragments;
        a probe labelling station configured to bind probes to the DNA bands;
        an imaging station configured to generate a first dataset based on an image of the DNA bands;
    a processor comprising:
        a matching logic configured to determine the first dataset matches a second dataset obtained from a database of preexisting datasets; and
        a device controller configured to cause a state of an access control device to change from a first state to a second state.

15. The access control system of claim 14, comprising a Southern blotting assembly configured to transfer the bands to a membrane.

16. The access control system of claim 14, wherein the matching logic is configured to determine whether the first dataset matches the second dataset within a match threshold.

17. The access control system of claim 14, comprising a restriction digestion assembly configured to perform restriction digestion using restriction enzymes to create minisatellites.

18. The access control system of claim 14, comprising an autoradiography station configured to irradiate the bands and probes to generate the first dataset from the bands.

19. The access control system of claim 14, comprising a priming station configured to bind labelled STR primers with a (PCR) polymerize chain reaction to the DNA sample to amplify DNA fragments and form labelled STRs (short tandem repeats).

20. The access control system of claim 14, comprising a laser assembly configured to illuminate the DNA bands with laser light of different frequencies.

21. The access control system of claim 14, wherein the imaging station is a detector configured to detect reflected light from the labelled primers bound to the bands.

22. The access control system of claim 21, wherein the first dataset comprises a frequency of reflected light and a relative position of the DNA band; the relative position based on a distance the STRs travelled during electrophoresis.

23. The access control system of claim 14, wherein the imaging station comprises autoradiography station configured to generate an autoradiograph of the DNA bands.

24. The access control system of claim 14, wherein the processor comprises silicone and the chip assembly comprises a microfluidics chip comprising PDMS (polydimethylsiloxane).

25. The access control system of claim 24, comprising:
   a wash station configured to clean components of the chip assembly; and
   a power source configured to provide electricity to the chip assembly and the processor.

26. The access control system of claim 14 comprising the access control device, said access control device configured to:
   display the first dataset on a tangible display;
   signal a gate or a lock to cause the gate or lock to open or close;
   grant or deny access to a computer or a physical location; or
   display a symbol designating whether the user's asserted identity matches a dataset within the database.

27. The processor of claim 14, comprising a biographic authentication logic containing:
   a biographic information collector configured to collect a first biographic information from the user; the user having a name and phone number; the biographic information comprising the user's name and user's phone number;
   a biographic association logic configured to associate the first biographic information with the first dataset;
   the database configured to store a second biographic information associated with a second datasets; and
   a biographic verification logic configured to verify that the second biographic information associated with the second dataset matches the first biographic information associated with the first dataset; and
   a marking logic configured to mark the user as verified for a time period.

* * * * *